US011452721B2

(12) United States Patent
Tejwani et al.

(10) Patent No.: US 11,452,721 B2
(45) Date of Patent: *Sep. 27, 2022

(54) FORMULATIONS OF PIMAVANSERIN

(71) Applicant: ACADIA Pharmaceuticals Inc., San Diego, CA (US)

(72) Inventors: Ravindra Tejwani, Monmouth Junction, NJ (US); Stephen Edward Abele, White Plains, NY (US); Emanuel Joseph Vizzotti, Millburn, NJ (US)

(73) Assignee: ACADIA Pharmaceuticals Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/693,830

(22) Filed: Mar. 14, 2022

(65) Prior Publication Data

US 2022/0193057 A1 Jun. 23, 2022

Related U.S. Application Data

(63) Continuation of application No. 17/080,731, filed on Oct. 26, 2020, which is a continuation of application No. 16/836,086, filed on Mar. 31, 2020, now Pat. No. 10,849,891, which is a continuation of application No. 16/571,554, filed on Sep. 16, 2019, now Pat. No. 10,646,480, which is a continuation of application No. 16/363,378, filed on Mar. 25, 2019, now Pat. No. 10,449,185, which is a continuation of application No. PCT/US2018/048096, filed on Aug. 27, 2018.

(60) Provisional application No. 62/552,300, filed on Aug. 30, 2017.

(30) Foreign Application Priority Data

Sep. 1, 2017 (SE) .................................. 1730232-4

(51) Int. Cl.
| | |
|---|---|
| *A61K 9/48* | (2006.01) |
| *A61K 31/4468* | (2006.01) |
| *A61K 9/16* | (2006.01) |
| *A61K 9/20* | (2006.01) |
| *A61K 47/38* | (2006.01) |

(52) U.S. Cl.
CPC ........ *A61K 31/4468* (2013.01); *A61K 9/1652* (2013.01); *A61K 9/1688* (2013.01); *A61K 9/1694* (2013.01); *A61K 9/2009* (2013.01); *A61K 9/2013* (2013.01); *A61K 9/2054* (2013.01); *A61K 9/485* (2013.01); *A61K 9/4808* (2013.01); *A61K 9/4833* (2013.01); *A61K 9/4858* (2013.01); *A61K 9/4866* (2013.01); *A61K 47/38* (2013.01); *C07B 2200/13* (2013.01)

(58) Field of Classification Search
CPC .. A61K 9/4833; A61K 9/4841; A61K 9/4883; A61K 9/4891
See application file for complete search history.

(56) References Cited

U.S. PATENT DOCUMENTS

| | | |
|---|---|---|
| 3,983,234 A | 9/1976 | Sayers |
| 4,138,492 A | 2/1979 | Noverola et al. |
| 4,255,432 A | 3/1981 | Kluge et al. |
| 4,332,804 A | 6/1982 | Clark |
| 4,353,900 A | 10/1982 | Clark |
| 4,353,901 A | 10/1982 | Clark |
| 4,367,232 A | 1/1983 | Boix-Igleasias et al. |
| 4,795,646 A | 1/1989 | Schlunken |
| 4,853,394 A | 8/1989 | King |
| 5,025,013 A | 6/1991 | Barreau |
| 5,214,055 A | 5/1993 | Peglion et al. |
| 5,216,165 A | 6/1993 | Mobilio et al. |
| 5,461,066 A | 10/1995 | Gericke et al. |
| 5,595,872 A | 1/1997 | Wetterau, II et al. |
| 5,621,010 A | 4/1997 | Sueda et al. |
| 5,707,798 A | 1/1998 | Brann |
| 5,795,894 A | 8/1998 | Shue |
| 5,837,730 A | 11/1998 | Javitt |
| 5,869,488 A | 2/1999 | Shue |
| 5,877,173 A | 3/1999 | Olney et al. |
| 5,912,132 A | 6/1999 | Brann |
| 5,955,281 A | 9/1999 | Brann |
| 6,107,324 A | 8/2000 | Behan |
| 6,140,509 A | 10/2000 | Behan |
| 6,150,393 A | 11/2000 | Behan |
| 6,358,698 B1 | 3/2002 | Weiner et al. |
| 6,451,343 B1 | 9/2002 | Glinecke et al. |
| 6,479,480 B1 | 11/2002 | Moyes |
| 6,486,153 B1 | 11/2002 | Castro Pineiro |
| 6,670,137 B2 | 12/2003 | VanMechelen et al. |
| 6,756,393 B2 | 6/2004 | Andersson et al. |
| 6,815,458 B2 | 11/2004 | Andersson et al. |
| 6,911,452 B2 | 6/2005 | Schlienger |
| 7,022,698 B2 | 4/2006 | Hamied et al. |
| 7,041,667 B1 | 5/2006 | Armour et al. |
| 7,087,593 B2 | 8/2006 | Kelly et al. |
| 7,115,634 B2 | 10/2006 | Thurieau et al. |
| 7,217,719 B2 | 5/2007 | Schlienger |
| 7,253,186 B2 | 8/2007 | Andersson et al. |
| 7,351,707 B2 | 4/2008 | Schlienger |
| 7,393,861 B2 | 7/2008 | Thurieau et al. |
| 7,476,682 B2 | 1/2009 | Andersson et al. |
| 7,538,222 B2 | 5/2009 | Andersson et al. |
| 7,601,740 B2 | 10/2009 | Weiner et al. |

(Continued)

FOREIGN PATENT DOCUMENTS

| | | |
|---|---|---|
| CA | 984843 A | 3/1976 |
| CN | 104844502 A | 8/2015 |

(Continued)

OTHER PUBLICATIONS

U.S. Appl. No. 09/800,096, Azacyclic compounds, filed Mar. 6, 2001, U.S. Pat. No. 6,815,458.

(Continued)

*Primary Examiner* — Micah Paul Young
(74) *Attorney, Agent, or Firm* — Goodwin Procter LLP

(57) ABSTRACT

Provided herein are capsules containing pimavanserin, processes for manufacturing said capsule, and pharmaceutical compositions containing pimavanserin.

13 Claims, 4 Drawing Sheets

(56) References Cited

U.S. PATENT DOCUMENTS

| | | |
|---|---|---|
| 7,659,285 B2 | 2/2010 | Weiner et al. |
| 7,713,995 B2 | 5/2010 | Weiner et al. |
| 7,732,462 B2 | 6/2010 | Weiner et al. |
| 7,732,615 B2 | 6/2010 | Thygesen et al. |
| 7,790,899 B2 | 9/2010 | Tolf et al. |
| 7,816,383 B1 | 10/2010 | Bradford et al. |
| 7,820,695 B2 | 10/2010 | Weiner et al. |
| 7,858,789 B2 | 12/2010 | Thurieau et al. |
| 7,863,296 B2 | 1/2011 | Weiner et al. |
| 7,868,176 B2 | 1/2011 | Thygesen et al. |
| 7,875,632 B2 | 1/2011 | Weiner et al. |
| 7,923,564 B2 | 4/2011 | Thygesen et al. |
| 7,994,193 B2 | 8/2011 | Weiner et al. |
| 8,008,323 B2 | 8/2011 | Weiner et al. |
| 8,110,574 B2 | 2/2012 | Thurieau et al. |
| 8,227,487 B2 | 7/2012 | Weiner et al. |
| 8,236,960 B2 | 8/2012 | Thygesen et al. |
| 8,377,959 B2 | 2/2013 | Weiner et al. |
| 8,618,130 B2 | 12/2013 | Weiner et al. |
| 8,921,393 B2 | 12/2014 | Weiner et al. |
| 9,050,343 B2 | 6/2015 | Peters et al. |
| 9,211,289 B2 | 12/2015 | Weiner et al. |
| 9,296,694 B2 | 3/2016 | Andersson et al. |
| 9,446,037 B2 | 9/2016 | Mills et al. |
| 9,486,453 B2 | 11/2016 | Javitt |
| 9,566,271 B2 | 2/2017 | Weiner et al. |
| 9,757,366 B2 | 9/2017 | Mills et al. |
| 9,765,053 B2 | 9/2017 | Andersson et al. |
| 10,028,944 B2 | 7/2018 | Weiner et al. |
| 10,449,185 B2 * | 10/2019 | Tejwani ................. A61K 9/485 |
| 10,517,860 B2 | 12/2019 | Parkinson |
| 10,525,046 B2 | 1/2020 | Weiner et al. |
| 10,597,363 B2 | 3/2020 | Carlos et al. |
| 10,646,480 B2 * | 5/2020 | Tejwani ................. A61K 9/4833 |
| 10,849,891 B2 * | 12/2020 | Tejwani ................. A61K 9/2054 |
| 10,953,000 B2 | 3/2021 | Parkinson |
| 10,981,870 B2 | 4/2021 | Carlos et al. |
| 10,981,871 B2 | 4/2021 | Carlos et al. |
| 11,135,211 B2 | 10/2021 | Burstein |
| 11,191,757 B2 | 12/2021 | Parkinson |
| 2002/0004513 A1 | 1/2002 | Andersson et al. |
| 2002/0156068 A1 | 10/2002 | Behan |
| 2002/0165225 A1 | 11/2002 | Kankan et al. |
| 2004/0006081 A1 | 1/2004 | Burrows |
| 2004/0106600 A1 | 6/2004 | Andersson et al. |
| 2004/0213816 A1 | 10/2004 | Weiner et al. |
| 2004/0229908 A1 | 11/2004 | Nelson |
| 2005/0014757 A1 | 1/2005 | Andersson et al. |
| 2005/0148018 A1 | 7/2005 | Weiner et al. |
| 2005/0244862 A1 | 11/2005 | Brann |
| 2005/0256108 A1 | 11/2005 | Schlienger |
| 2005/0261278 A1 | 11/2005 | Weiner et al. |
| 2005/0261340 A1 | 11/2005 | Weiner et al. |
| 2005/0288328 A1 | 12/2005 | Weiner et al. |
| 2006/0094758 A1 | 5/2006 | Andersson et al. |
| 2006/0106063 A1 | 5/2006 | Thhygesen et al. |
| 2006/0111399 A1 | 5/2006 | Thhygesen et al. |
| 2006/0194778 A1 | 8/2006 | Andersson et al. |
| 2006/0194834 A1 | 8/2006 | Andersson et al. |
| 2006/0199794 A1 | 9/2006 | Schlienger |
| 2006/0199818 A1 | 9/2006 | Andersson et al. |
| 2006/0199842 A1 | 9/2006 | Weiner et al. |
| 2006/0204486 A1 | 9/2006 | Pyke et al. |
| 2006/0205710 A1 | 9/2006 | Schlienger |
| 2006/0205722 A1 | 9/2006 | Andersson et al. |
| 2006/0205780 A1 | 9/2006 | Thygesen et al. |
| 2006/0205781 A1 | 9/2006 | Thygesen et al. |
| 2006/0264465 A1 | 11/2006 | Weiner et al. |
| 2006/0264466 A1 | 11/2006 | Weiner et al. |
| 2006/0286610 A1 | 12/2006 | Brann |
| 2006/0292606 A1 | 12/2006 | Brann |
| 2007/0260064 A1 | 11/2007 | Tolf et al. |
| 2007/0264330 A1 * | 11/2007 | Ragnar-Tolf ......... A61K 9/2059 424/464 |
| 2008/0051429 A1 | 2/2008 | Van Kammen et al. |
| 2008/0280886 A1 | 11/2008 | Gant et al. |
| 2009/0053329 A1 | 2/2009 | Peters et al. |
| 2009/0082342 A1 | 3/2009 | Uldam et al. |
| 2009/0082388 A1 | 3/2009 | Hacksell |
| 2009/0186921 A1 | 7/2009 | Andersson et al. |
| 2014/0018348 A1 | 1/2014 | Javitt |
| 2014/0162942 A1 | 6/2014 | Ghosal et al. |
| 2014/0221395 A1 | 8/2014 | Dhanoa |
| 2014/0329903 A1 | 11/2014 | Burstein et al. |
| 2014/0349976 A1 | 11/2014 | Hacksell et al. |
| 2015/0231126 A1 | 8/2015 | Peters |
| 2015/0313888 A1 | 11/2015 | Mills et al. |
| 2016/0237036 A1 | 8/2016 | Andersson et al. |
| 2018/0037549 A1 | 2/2018 | Biljan |
| 2019/0030015 A1 | 1/2019 | Weiner et al. |
| 2019/0047955 A1 | 2/2019 | Carlos et al. |
| 2019/0117636 A1 | 4/2019 | Burstein |
| 2019/0216791 A1 | 7/2019 | Tejwani et al. |
| 2019/0231767 A1 | 8/2019 | Parkinson |
| 2019/0240211 A1 | 8/2019 | Parkinson |
| 2020/0009122 A1 | 1/2020 | Tejwani et al. |
| 2020/0061045 A1 | 2/2020 | Burstein |
| 2020/0078346 A1 | 3/2020 | Parkinson |
| 2020/0165202 A1 | 5/2020 | Carlos et al. |
| 2020/0181087 A1 | 6/2020 | Carlos et al. |
| 2020/0222381 A1 | 7/2020 | Tejwani et al. |
| 2020/0237739 A1 | 7/2020 | Coate et al. |
| 2020/0323836 A1 | 10/2020 | Weiner et al. |
| 2021/0077479 A1 | 3/2021 | Tejwani et al. |
| 2021/0161880 A1 | 6/2021 | Foff |
| 2021/0283118 A1 | 9/2021 | Tejwani et al. |
| 2022/0000852 A1 | 1/2022 | Burstein |
| 2022/0016101 A1 | 1/2022 | Burstein et al. |
| 2022/0024871 A1 | 1/2022 | Carlos et al. |

FOREIGN PATENT DOCUMENTS

| | | |
|---|---|---|
| CN | 104961672 A | 10/2015 |
| CN | 105111135 A | 12/2015 |
| CN | 105153016 A | 12/2015 |
| CN | 105418460 A | 3/2016 |
| CN | 105481757 A | 4/2016 |
| CN | 105820110 A | 8/2016 |
| CN | 106543072 A | 3/2017 |
| EP | 0005318 B1 | 11/1979 |
| EP | 0061333 B1 | 9/1982 |
| EP | 0260070 B1 | 3/1988 |
| EP | 0379441 A1 | 7/1990 |
| EP | 0548015 B1 | 6/1993 |
| EP | 0625507 B1 | 11/1994 |
| EP | 1576985 A1 | 9/2005 |
| HU | 157325 | 3/1998 |
| JP | 51052176 | 5/1976 |
| JP | 52085174 A | 7/1977 |
| WO | WO-9427967 A1 | 12/1994 |
| WO | WO-9708166 A1 | 3/1997 |
| WO | WO-9711940 A1 | 4/1997 |
| WO | WO-9738665 A2 | 10/1997 |
| WO | WO-9738984 A1 | 10/1997 |
| WO | WO-9811128 A1 | 3/1998 |
| WO | WO-9817646 A1 | 4/1998 |
| WO | WO-98/44921 A1 | 10/1998 |
| WO | WO-98/50534 A1 | 11/1998 |
| WO | WO-9952927 A1 | 10/1999 |
| WO | WO-2000/020636 A1 | 4/2000 |
| WO | WO-0023076 A1 | 4/2000 |
| WO | WO-0056335 A1 | 9/2000 |
| WO | WO-0059497 A1 | 10/2000 |
| WO | WO-0069810 A1 | 11/2000 |
| WO | WO-2001/029008 A1 | 4/2001 |
| WO | WO-0144191 A1 | 6/2001 |
| WO | WO-0166521 A1 | 9/2001 |
| WO | WO-0187839 A1 | 11/2001 |
| WO | WO-2001089498 A2 | 11/2001 |
| WO | WO-0224649 A1 | 3/2002 |
| WO | WO-2002038142 A2 | 5/2002 |
| WO | WO-02076464 A1 | 10/2002 |
| WO | WO-02079186 A2 | 10/2002 |
| WO | WO-03057698 A2 | 7/2003 |

(56) References Cited

FOREIGN PATENT DOCUMENTS

| WO | WO-03062206 A2 | 7/2003 |
|---|---|---|
| WO | WO-03070246 A1 | 8/2003 |
| WO | WO-03086400 A1 | 10/2003 |
| WO | WO-04000808 A2 | 12/2003 |
| WO | WO-04039322 A2 | 5/2004 |
| WO | WO-04064753 A2 | 8/2004 |
| WO | WO-2004064738 A2 | 8/2004 |
| WO | WO-05053796 A1 | 6/2005 |
| WO | WO-05063254 A2 | 7/2005 |
| WO | WO-05112927 A1 | 12/2005 |
| WO | WO-2006036874 A1 | 4/2006 |
| WO | WO-2006037043 A1 | 4/2006 |
| WO | WO-06104826 A2 | 10/2006 |
| WO | WO-2007124136 A1 | 11/2007 |
| WO | WO-2007133802 A2 | 11/2007 |
| WO | WO-2008116024 A2 | 9/2008 |
| WO | WO-2008141057 A1 | 11/2008 |
| WO | WO-2008144326 A2 | 11/2008 |
| WO | WO-2008144665 A1 | 11/2008 |
| WO | WO-2009035473 A2 | 3/2009 |
| WO | WO-2009039460 A2 | 3/2009 |
| WO | WO-2009039461 A2 | 3/2009 |
| WO | WO-2010111353 A1 | 9/2010 |
| WO | WO-2011047341 A2 | 4/2011 |
| WO | WO-2011085216 A2 | 7/2011 |
| WO | WO-2014085362 A1 | 6/2014 |
| WO | WO-2015/087283 A1 | 6/2015 |
| WO | WO-2016201373 A1 | 12/2016 |
| WO | WO-2017011767 A2 | 1/2017 |
| WO | WO-2017015272 A1 | 1/2017 |
| WO | WO-2017165635 A1 | 9/2017 |
| WO | WO-2017172757 A1 | 10/2017 |
| WO | WO-2018118626 A1 | 6/2018 |
| WO | WO-2018200977 A1 | 11/2018 |
| WO | WO-2019046167 A1 | 3/2019 |
| WO | WO-2019177973 A1 | 9/2019 |
| WO | WO-2020092618 A1 | 5/2020 |
| WO | WO-2021016369 A1 | 1/2021 |
| WO | WO-2021030607 A1 | 2/2021 |

OTHER PUBLICATIONS

U.S. Appl. No. 10/409,782, Azacyclic compounds, filed Apr. 7, 2003, U.S. Pat. No. 6,756,393.
U.S. Appl. No. 13/053,079, Methods of treatment using selective 5-HT2A inverse agonists, filed Mar. 21, 2011, U.S. Pat. No. 9,765,053.
U.S. Appl. No. 14/628,156, Azacyclic compounds, filed Feb. 20, 2015, U.S. Pat. No. 9,296,694.
U.S. Appl. No. 10/759,564, Selective serotonin 2A/2C receptor inverse agonists as therapeutics for neurodegenerative diseases, filed Jan. 15, 2004, U.S. Pat. No. 7,601,740.
U.S. Appl. No. 11/416,527, Selective Serotonin 2A/2C Receptor Inverse Agonists as Therapeutics for Neurodegenerative Diseases, filed May 3, 2006 2006, U.S. Pat. No. 7,732,462.
U.S. Appl. No. 11/416,855, Selective serotonin 2A/2C receptor inverse agonists as therapeutics for neurodegenerative diseases, filed May 3, 2006, U.S. Pat. No. 7,659,285.
U.S. Appl. No. 11/416,594, Selective serotonin 2A/2C receptor inverse agonists as therapeutics for neurodegenerative diseases, filed May 3, 2006, U.S. Pat. No. 7,713,995.
U.S. Appl. No. 12/759,662, Selective serotonin 2A/2C receptor inverse agonists as therapeutics for neurodegenerative diseases, filed Apr. 13, 2010, U.S. Pat. No. 7,994,193.
U.S. Appl. No. 12/759,664, Selective serotonin 2A/2C receptor inverse agonists as therapeutics for neurodegenerative diseases, filed Apr. 13, 2010, U.S. Pat. No. 8,008,323.
U.S. Appl. No. 13/169,893, Selective serotonin 2A/2C receptor inverse agonists as therapeutics for neurodegenerative diseases, filed Jun. 27, 2011, U.S. Pat. No. 8,227,487.
U.S. Appl. No. 13/539,011, Selective serotonin 2A/2C receptor inverse agonists as therapeutics for neurodegenerative diseases, filed Jun. 29, 2012, U.S. Pat. No. 8,377,959.
U.S. Appl. No. 13/750,778, Selective serotonin 2A/2C receptor inverse agonists as therapeutics for neurodegenerative diseases, filed Jan. 25, 2013, U.S. Pat. No. 8,618,130.
U.S. Appl. No. 14/086,838, Selective serotonin 2A/2C receptor inverse agonists as therapeutics for neurodegenerative diseases, filed Nov. 21, 2013, U.S. Pat. No. 8,921,393.
U.S. Appl. No. 14/537,793, Selective serotonin 2A/2C receptor inverse agonists as therapeutics for neurodegenerative diseases, filed Nov. 10, 2014, U.S. Pat. No. 9,211,289.
U.S. Appl. No. 14/935,246, Selective serotonin 2A/2C receptor inverse agonists as therapeutics for neurodegenerative diseases, filed Nov. 6, 2015, U.S. Pat. No. 9,566,271.
U.S. Appl. No. 15/397,582, Selective serotonin 2A/2C receptor inverse agonists as therapeutics for neurodegenerative diseases, filed Jan. 3, 2017, U.S. Pat. No. 10,028,944.
U.S. Appl. No. 16/019,485, Selective serotonin 2A/2C receptor inverse agonists as therapeutics for neurodegenerative diseases, filed Jun. 26, 2018, U.S. Pat. No. 10,525,046.
U.S. Appl. No. 17/474,816, Selective serotonin 2A/2C receptor inverse agonists as therapeutics for neurodegenerative diseases, filed Sep. 14, 2021, Pending.
U.S. Appl. No. 10/850,819, Selective serotonin receptor inverse agonists as therapeutics for disease, filed May 21, 2004, U.S. Pat. No. 7,820,695.
U.S. Appl. No. 11/134,769, Selective serotonin receptor inverse agonists as therapeutics for disease, filed May 20, 2005, U.S. Pat. No. 7,863,296.
U.S. Appl. No. 12/378,385, Selective serotonin receptor inverse agonists as therapeutics for disease, filed Feb. 11, 2009, U.S. Pat. No. 7,875,632.
U.S. Appl. No. 11/235,558, N-(4-fluorobenzyl)-N-(1-methylpiperidin-4-yl)-N'-(4-(2-methylpropyloxy)phenylmethyl)carbamide and its tartrate salt and crystalline forms, filed Sep. 26, 2005, U.S. Pat. No. 7,732,615.
U.S. Appl. No. 11/235,381, Salts of N-(4-fluorobenzyl)-N-(1-methylpiperidin-4-yl)-N'-(4-(2-methylprop-yloxy)phenylmethyl)carbamide and their preparation, filed Sep. 26, 2005, U.S. Pat. No. 7,868,176.
U.S. Appl. No. 12/795,547, Synthesis of N-(4-fluorobenzyl)-N-(1-methylpiperidin-4-yl)-N'-(4-(2-methylpropyloxy)phenylmethyl)carbamide and its tartrate salt and crystalline forms, filed Jun. 7, 2010, U.S. Pat. No. 7,923,564.
U.S. Appl. No. 13/081,427, Synthesis of N-(4-fluorobenzyl)-N-(1-methylpiperidin-4-yl)-N'-(4-(2-methylpropyloxy)phenylmethyl)carbamide and its tartrate salt and crystalline forms, filed Apr. 6, 2011, U.S. Pat. No. 8,236,960.
U.S. Appl. No. Synthesis of N-(4-fluorobenzyl)-N-(1-methylpiperidin-4-yl)-N'-(4-(2-methylpropyloxy)phenylmethyl)carbamide and its tartrate salt and crystalline forms, filed May 15, 2007, U.S. Pat. No. 7,790,899.
U.S. Appl. No. 13/754,769, Combination of pimavanserin and risperidone for the treatment of psychosis, filed Jan. 30, 2013, U.S. Pat. No. 9,050,343.
U.S. Appl. No. 14/647,438, Methods for the treatment of Parkinson's disease psychosis using pimavanserin, filed May 26, 2015, U.S. Pat. No. 9,446,037.
U.S. Appl. No. 15/246,412, Methods for the treatment of Parkinson's disease psychosis using pimavanserin, filed Aug. 24, 2016, U.S. Pat. No. 9,757,366.
U.S. Appl. No. 15/744,636, Methods for preparing N-(4-fluorobenzyl)-N-(1-methylpiperidin-4-yl)-N'-(4-(2-methylpropyloxy)phenylmethyl)carbamide and its tartrate salt and polymorphic form, filed Jan. 12, 2018, U.S. Pat. No. 10,597,363.
U.S. Appl. No. 16/743,607, Methods for preparing N-(4-fluorobenzyl)-N-(1-methylpiperidin-4-yl)-N'-(4-(2-methylpropyloxy)phenylmethyl)carbamide and its tartrate salt and polymorphic form, filed Jan. 15, 2020, U.S. Pat. No. 10,981,870.
U.S. Appl. No. 16/686,809, Methods for preparing N-(4-fluorobenzyl)-N-(1-methylpiperidin-4-yl)-N'-(4-(2-methylpropyloxy)phenylmethyl)carbamide and its tartrate salt and polymorphic form, filed Feb. 10, 2020, U.S. Pat. No. 10,981,871.
U.S. Appl. No. 17/203,266, Methods for preparing N-(4-fluorobenzyl)-N-(1-methylpiperidin-4-yl)-N'-(4-(2-

(56) References Cited

OTHER PUBLICATIONS methylpropyloxy)phenylmethyl)carbamide and its tartrate salt and polymorphic form, filed Mar. 16, 2021, Pending, 20220024871.
U.S. Appl. No. 17/176,723, 5-HT2A serotonin receptor inverse agonists or antagonists for use in reducing amyloid-beta peptides and accumulation of amyloid plaques, filed Feb. 16, 2021, Pending, 20220000852.
U.S. Appl. No. 16/087,604, Combination of pimavanserin and cytochrome p450 modulators, filed Sep. 21, 2018, U.S. Pat. No. 10,953,000.
U.S. Appl. No. 16/379,169, Combination of pimavanserin and cytochrome p450 modulators, filed Apr. 9, 2019, U.S. Pat. No. 10,517,860.
U.S. Appl. No. 16/684,883, Combination of pimavanserin and cytochrome p450 modulators, filed Nov. 19, 2019, U.S. Pat. No. 11,191,757.
U.S. Appl. No. 17/518,776, Combination of pimavanserin and cytochrome p450 modulators, filed Nov. 4, 2021, Pending.
U.S. Appl. No. 16/607,234, Pimavanserin for Treating Impulse Control Disorder, filed Oct. 22, 2019, U.S. Pat. No. 11,135,211.
U.S. Appl. No. 17/412,659, Pimavanserin for Treating Impulse Control Disorder, filed Aug. 26, 2021, Pending.
U.S. Appl. No. 16/471,543, Methods for the Treatment of Alzheimer's Disease Psychosis Using Pimavanserin, filed Jun. 19, 2019, Pending, 20200237739.
U.S. Appl. No. 16/363,378, Formulations of Pimavanserin, filed Mar. 25, 2019, U.S. Pat. No. 10,449,185.
U.S. Appl. No. 16/571,554, Formulations of Pimavanserin, filed Sep. 16, 2019, U.S. Pat. No. 10,646,480.
U.S. Appl. No. 16/836,086, Formulations of Pimavanserin, filed Mar. 31, 2020, U.S. Pat. No. 10,849,891.
U.S. Appl. No. 17/080,731, Formulations of Pimavanserin, filed Oct. 26, 2020, Pending, 20210283118.
U.S. Appl. No. 17/290,479, Methods of Treating Depression, Anxiety and Sexual Dysfunction Using the Compound Primavanserin, filed Apr. 30, 2021, Pending, 20220016101.
U.S. Appl. No. 17/108,623, Methods for Treating Dementia Related Psychosis, filed Dec. 1, 2020, Pending, 20210161880.
U.S. Appl. No. 17/635,459, Pimavanserin for Treating Neurodegenerative Diseases, filed Feb. 15, 2022, Pending.
U.S. Appl. No. 17/629,098, Pimavanserin for Treating Schizophrenia for Treating Psychosis Secondary to Neurodegenerative Disorders or Depressive Disorder, filed Jan. 21, 2022, Pending.
"ACP-103," *Drugs of the Future, Prous Science* (2006) vol. 31, No. 11, pp. 939-943.
"NUPLAZID™ (pimavanserin) Sponsor Background Information for a Meeting of the Psychopharmacologic Drugs Advisory Committee on Mar. 29, 2016," Acadia Pharmaceuticals Inc., 2016. Retrieved from the Internet (URL): <https://www.fda.gov/downloads/advisorycommittees/committeesmeetingmaterials/drugs/psychopharmacologicdrugsadvisorycommittee/ucm492453.pdf> (173 pages).
"Pimavanserin (Nuplazid) for parkinson's disease psychosis," Medical Letter on Drugs and Therapeutics, New Rochelle, NY, US (Jun. 2016) vol. 58, pp. 74-75.
Aarsland et al., "Decreased burden among caregivers of patients with Parkinson's disease psychosis (PDP) treated with pimavanserin, a selective 5-HT2A inverse agonist," (Meeting Abstract) *Neurology* (2015) vol. 84, No. 14, Suppl P6.044.
Abbas et al., "Pimavanserin tartrate: a 5-HT2A inverse agonist with potential for treating various neuropsychiatric disorders," *Expert Opinion on Pharmacotherapy* (2008) vol. 9, No. 18, pp. 3251-3259.
Acadia Pharmaceuticals, "Acadia Pharmaceuticals Announces FDA approval of New Dosing Formulation and Strength for NUPLAZID (Pimavanserin)," Press Release, San Diego (CA) Jun. 29, 2018. Retrieved from the internet (URL): http://ir.acadia-pharm.com/phoenix.zhtml?c=125180&p=irol-newsArticle&ID=2356605 (3 pages).
Adam, et al., "Effects of repeated ritanserin on middle-aged poor sleepers," *Psychopharmacology* (1989) 99:219-221.

Aizenstein et al., "Frequent Amyloid Deposition Without Significant Cognitive Impairment Among the Elderly," Arch. Neurol. 65(11):1509-1517 (2008).
Akin, et al., "Decreased serotonin 5-HT 2A receptor-stimulated phosphoinositide signaling in fibroblasts from melancholic depressed patients," *Neuropsychopharmacology* (2004) 29:2081-2087.
Anonymous, "Use of Liquids and/or Soft Foods as Vehicles for Drug Administration: General Considerations for Selection and In Vitro Methods for Product Quality Assessments Guidance for Industry," Jul. 13, 2018 (Jul. 13, 2018), XP055676101, Retrieved from the Internet: URL:https://www.fda.gov/media/114872/downl <http://www.fda.gov/media/114872/downl> oad [retrieved on Mar. 12, 2020].
Antunes, et al., "The novel object recognition memory: neurobiology, test procedure, and its modifications," *Cogn. Process* (2012) 13:93-110.
Bakshi, et al., "Clozapine antagonizes phencyclidine-induced deficits in sensorimotor gating of the startle response," *The Journal of Pharmacology and Experimental Therapeutics* (1994) 271(2)787-794.
Basha, A., "Synthesis of N, N'-disubstituted Ureas from Carbamates," Tetrahedron Letters 29(21):2525-2526 (1988).
Bekris et al. "Cerebrospinal Fluid Ab42 Levels and APP processing pathway genes in Parkinson's disease," Movement Disorders, 2015, vol. 30, No. 7, pp. 936-944, 2015.
Bennett, et al., "Suppression of dyskinesias in advanced Parkinson's disease. II. Increasing daily clozapine doses suppress dyskinesias and improve parkinsonism symptoms," *Neurology* (1993) 43:1551-1554.
Bhana et al., "A Review of its Use in the Management of the Behavioural and Psychological Symptoms of Dementia," Drugs & Aging 16(6):451-471 (2000).
Biagi, et al., "1,2,3-Triazoles: Structural changes on two effective inhibitors of the prostaglandin synthesis in vitro," *Farmaco Ed. Sci.* (1988) 43:597-611.
Bibbiani, et al., "Serotonin 5-HT1A agonist improves motor complications in rodent and primate parkinsonian models," *Neurology* (2001) 57:1829-1834.
Blakley, et al., "Bidirectional changes in ethanol consumption in rats with site-specific antisense down-regulation of 5-hydroxytryptamine2A receptors in brain," *The Journal of Pharmacology and Experimental Therapeutics* (2001) 299(1):277-289.
Blier, et al., "Potential mechanisms of action of atypical antipsychotic medications in treatment-resistant depression and anxiety," *J. Clin. Psychiatry* (2005) 66(suppl 8):30-40.
Blier, et al., "Putative mechanisms of action of antidepressant drugs in affective and anxiety disorders and pain," *Journal of Psychiatry & Neuroscience* (2001) 26(1):37-43.
Bogolubsky et al., "Bis(2,2,2-trifluoroethyl) carbonate as a condensing agent in one-pot parallel synthesis of unsymmetrical aliphatic ureas," (2014), pages S1-S67. Retrieved from URL: http://pubs.acs.org/doi/suppl/10.1021/co500025f/suppl_file co500025f_si_001.pdf, Table S2, pp. S9, entry 47.
Bogolubsky et al., "Bis(2,2,2-trifluoroethyl) carbonate as a condensing agent in one-pot parallel synthesis of unsymmetrical aliphatic ureas," *ACS Combinatorial Science* (2014) vol. 16, Issue 6, pp. 303-308.
Bond et al., "Physiological effects of inverse agonists in transgenic mice with myocardial overexpression of the beta-adrenoceptor," *Nature* (1995) 374:272-276.
Borman et al., "5-HT2B receptors play a key role in mediating the excitatory effects of 5-HT in human colon in vitro," *Br. J. Pharmacol.* (2002) vol. 135, No. 5, pp. 1144-1151.
Brann, M. R. "Identification of ligands by selective amplification of cells transfected with receptors and marker enzymes," *Chemical Abstracts* (1998) 128: 111548.
Buddhala et al. "Correlation between descreased CSF a-synuclein and Ab1-42 in Parkinson disease," Neurobiology of Aging, 2015, vol. 36, pp. 476-484, 2015.
Chaturvedi, D., "Perspectives on the Synthesis of Organic Carbamates," Tetrahedron 68:15-45 (2012).
Chaturvedi, D., "Recent Developments on the Carbamation of Amines," Curr. Org. Chem. 15:1593-1624 (2011).

(56) References Cited

OTHER PUBLICATIONS

Choi et al., "5HT2B receptor-mediated serotonin morphogenic functions in mouse cranial neural crest and myocardiac cells," *Development* (1997) vol. 124, pp. 1745-1755.

Cirrito et al., "Serotonin signaling is associated with lower amyloid-p levels and plaques in transgenic mice and humans," *PNAS* (2011) vol. 108, No. 36, pp. 14968-14973.

Colovic et al., "Acetylcholinesterase Inhibitors: Pharmacology and Toxicology," Current Neuropharmacology 11:315-335 (2013).

Cummings et al., "Pimavanserin for patients with Parkinson's disease psychosis: a randomised, placebo-controlled phase 3 trial," *Lancet* (2014) vol. 383, pp. 533-540.

Cummings et al., "Pimavanserin: Potential Treatment for Dementia-Related Psychosis." J. Prev. Alzheimers Dis. 5(4): 253-258 (2018).

Cunningham et al., "Serotonin at the Nexus of Impulsivity and Cue Reactivity in Cocaine Addiction," *Neuropharmacology* 76(0 0): 460-478.

Database CA [online] Chemical Abstracts Service, Columbus, Ohio, US; 2016, Wang et al., "Intermediate of pimavanserin and its analog, preparation method thereof and preparation method of pimavanserin and its analog," XP002761533, retrieved from STN Database accession No. 2016:451070 (reference date: Mar. 23, 2016).

Database CA [online] Chemical Abstracts Service, Columbus, Ohio, US; 2016, Zheng, Xuchun et al: "A process for preparing pimavanserin tartrate," XP002761538, retrieved from STN Database accession No. 2016:1261850 (reference date: Aug. 3, 2016).

Database WPI Week 201622, Derwent Publications Ltd., London, GB; AN 2016-17318M, XP002761536 (reference date: Aug. 19, 2015).

Database WPI Week 201623, Derwent Publications Ltd., London, GB; AN 2015-708058, XP002761532 (reference date: Oct. 7, 2015).

Database WPI Week 201635, Derwent Publications Ltd., London, GB; AN 2016-02257F, XP002761534 (reference date: Dec. 2, 2015).

Database WPI Week 201640, Derwent Publications Ltd., London, GB; AN 2016-01442V, XP002761535 (reference date: Dec. 16, 2015).

Database WPI Week 201641, Derwent Publications Ltd., London, GB; AN 2016-24419S, XP002761537 (reference date: Apr. 13, 2016).

DeClerck, et al., "Increase in slow-wave sleep in humans with the serotonin-S2 antagonist ritanserin," *Current Therapeutic Research* (1987) 41(4):427-432.

Delecluse, et al., "A case of tardive tremor successfully treated with clozapine," *Movement Disorders* (1998) 13(5):846-847.

Dine et al., "One-Pot, Solvent-Free Access to Unsymmetrical Ureas by Palladium-Catalysed Reductive Alkylation Using Molecular Hydrogen," Eur. J. Chem., 5445-5454 (2013).

Dube et al., "Carbonyldiimidazole-Mediated Lossen Rearrangement." Org. Lett. 11(24):5622-5625 (2009).

Dunn, et al., "Analgetic and antiinflammatory 7-aroylbenzofuran-5-ylacetic acids and 7-aroylbenzothiophene-5-ylacetic acids," *J. Med. Chem.* (1986) 29:2326-2329.

Durif, et al., "Low-dose clozapine improves dyskinesias in Parkinson's disease," *Neurology* (1997) 48:658-662.

Eichelbaum, et al., "Influence of pharmacogenetics on drug disposition and response," *Clinical and Experimental Pharmacology and Physiology* (1996) 23:983-985.

Everett, et al., "L-Dopa: Effect on concentrations of dopamine, norepinephrine, and serotonin in brains of mice," *Science* (1970) 168:849-850.

Factor, et al. "Clozapine for the treatment of drug-induced psychosis in Parkinson's disease: Results of the 12 week open label extension in the PSYCLOPS trial," *Movement Disorders* (2001) 16(1):135-139.

Factor, et al., "Clozapine prevents recurrence of psychosis in Parkinson's disease," *Movement Disorders* (1992) 7(2):125-131.

Fava, M. et al. "A Phase 2, Randomized, Double-Blind, Placebo-Controlled Study of Adjunctive Pimavanserin in Patients with Major Depressive Disorder and an Inadequate Response to Therapy (CLARITY)." J Clin Psychiatry. Sep. 24, 2019;80(6) (13 pages).

Fitzgerald et al., "Possible Role of Valvular Serotonin 5-HT2B Receptors in the Cardiopathy Associated with Fenfluramine," *Molecular Pharmacol.* (1999) vol. 57, pp. 75-81.

Friedman et al., "A Multi-Center, Placebo-Controlled, Double-Blind Trial to Examine the Safety and Efficacy of Pimavanserin in the Treatment of Psychosis in Parkinson's Disease," *Neurology* (2010) vol. 74, No. 9, Suppl. 2, pp. A299.

Friedman, et al., "Atypical antipsychotics in the treatment of drug-induced psychosis in Parkinson's disease," *Movement Disorders* (2000) 15(2):201-211.

Friedman, et al., "Low-dose clozapine for the treatment of drug-induced psychosis in Parkinson's disease," N. *Engl. J. Med.* (1999) 340(10):757-763.

Friedman, J. H. "Clozapine treatment of psychosis in patients with tardive dystonia: Report of three cases," *Movement Disorders* (1994) 9(3):321-324.

Gillman, P. K. "Monoamine oxidase inhibitors, opioid analgesics and serotonin toxicity," *British Journal of Anaesthesia* (2005) 95(4):434-441.

Goldman et al., "Genetic counseling and testing for Alzheimer disease: Joint practice guidelines of the American College of Medical Genetics and the National Society of Genetic Counselors," *Genetics in Medicine* (2011) vol. 13, No. 6, pp. 597-605.

Hacksell et al., 2014, "On the Discovery and Development of Pimavanserin: A Novel Drug Candidate for Parkinson's Psychosis," Neurochem. Res., vol. 39, pp. 2008-2017.

Han et al., "Synthesis of Carbamates and Ureas Using Zr(IV)-Catalyzed Exchange Processes," Organic Letters 9(8): 1517-1520 (2007).

Hatoum, H. T. et al., "The Use of the Occupational Disruptiveness Scale of the Neuropsychiatric Inventory-Nusing Home Version to Measure the Impact of Rivastigmine on the Disruptive Behavior of Nursing Home Residents with Alzheimer's Disease," *Journal of the American Medical Directors Association* (2005) vol. 6, No. 4, pp. 238-245.

Highlights of Prescribing Information Nuplazid™ (pimavanserin), Revised Apr. 2016. Retrieved from the Internet (URL): https://www.accessdata.fda.gov/drugsatfda_docs/label/2016/207318lbl.pdf (14 pages).

Highlights of Prescribing Information Nuplazid® (pimavanserin), Revised Jun. 2018. Retrieved from the Internet (URL): https://www.accessdata.fda.gov/drugsatfda_docs/label/2018/207318s005lbl.pdf (15 pages).

Highlights of Prescribing Information Nuplazid® (pimavanserin), Revised Mar. 2018. Retrieved from the Internet (URL): https://www.accessdata.fda.gov/drugsatfda_docs/label/2018/207318s002s004lbl.pdf (15 pages).

Idzikowski, et al. 1991. A dose response study examining the effects of ritanserin on human slow wave sleep. Br. J. Clin. Pharmac., 31:193-196.Idzikowski, et al., "A dose response study examining the effects of ritanserin on human slow wave sleep," *Br. J. Clin. Pharmac.* (1991) 31:193-196.

International Search Report and Written Opinion for International Application No. PCT/US2013/071792, dated, Jan. 1, 2014 (9 pages).

International Search Report and Written Opinion in corresponding PCT Application PCT/US2016/042933 dated Oct. 14, 2016 (13 pages).

International Search Report and Written Opinion in corresponding PCT Patent Application No. PCT/US08/057557 dated Oct. 24, 2008 (10 pages).

International Search Report and Written Opinion in corresponding PCT Patent Application No. PCT/US2017/023795 dated May 29, 2017 (11 pages).

International Search Report and Written Opinion in corresponding PCT Patent Application No. PCT/US2017/024526 dated Jul. 5, 2017 (18 pages).

International Search Report and Written Opinion in corresponding PCT Patent Application No. PCT/US2017/066340 dted Mar. 5, 2018 (13 pages).

(56) References Cited

OTHER PUBLICATIONS

International Search Report and Written Opinion in corresponding PCT Patent Application No. PCT/US2018/029831 dated Jul. 11, 2018 (10 pages).
International Search Report and Written Opinion in corresponding PCT Patent Application No. PCT/US2018/048096 dated Oct. 30, 2018 (12 pages).
International Search Report and Written Opinion of the International Searching Authority for International Application No. PCT/US2019/021618 dated Jun. 12, 2019 (10 pages).
International Search Report and Written Opinion of the International Searching Authority for International Application No. PCT/US2019/058927 dated Jan. 23, 2020 (16 pages).
International Search Report and Written Opinion of the International Searching Authority for International Application No. PCT/US2020/043103 dated Dec. 18, 2020 (12 pages).
International Search Report and Written Opinion of the International Searching Authority for International Application No. PCT/US2020/46212 dated Oct. 23, 2020 (10 pages).
International-type Search Report by International Searching Authority for SE1630067-5 dated Sep. 23, 2016 (18 pages).
Ito et al., "Prediction of Human Drug Clearance from in Vitro and Preclinical Data Using Physiologically Based and Empirical Approaches," Pharm. Res., (2005) vol. 22, No. 1, pp. 103-112.
Kalgutkar, et al., "Selective inhibitors of monoamine oxidase (MAO-A and MAO-B) as probes of its catalytic site and mechanism," *Medicinal Research Reviews* (1995) 15(4)325-388.
Katritzky et al., Chapter V. "Reaction of Amines with Carbamic Acid Esters," Comprehensive Organic Functional Group Transmformations, pp. 501-502 (1995).
Kennedy et al., "The BACE1 inhibitor verubecestat (MK-8931) reduces CNS β-amyloid in animal models and in Alzheimer's disease patients," Sci. Transl. Med. 8, 363ra150 13 pages (2016).
Kondo et al., "Novel Ruthenium-Complex Catalyzed Synthesis of Ureas from Formamides and Amines," Organometallics 16:2562-2570 (1997).
Kotachi et al., "Ruthenium catalysed N.N'-Diarylurea Synthesis from N-Aryl Substituted Formamides and Aminoarenes," J. Chem. Soc., Chem. Comm., 7:549-550 (1990).
Lane et al., "Alzheimer's Disease," Eur. J. Neurol. 25:59-70 (2018).
Lashley et al. "Cortical a-synuclein load is associated with amyloid-b plaque burden in subset of Parkinson disease patients," Acta Neuropathol. 2008, 115, 417-425.
Leysen, et al. "Serotonergic component of neuroleptic receptors," *Nature* (1978) 272:168-171.
Liechti, et al., "Effects of MDMA (ecstasy) on prepulse inhibition and habituation of startle in humans after pretreatment with Citalopram, Haloperidol, or Ketanserin," *Neuropsychopharmacology* (2001) 24(3):240-252.
Linder, et al. "Pharmacogenetics: A laboratory tool for optimizing therapeutic efficiency," *Clinical Chemistry* (1997) 43(2):254-266.
Loudon et al., "Conversion of Aliphatic Amides into Amines with [I,I-Bis(trifluoroacetoxy)iodo]benzene. 1. Scope of Reaction," J. Org. Chem. 49:4272-4276 (1984).
Marek et al., "The Selective 5-HT2A receptor Antagonist MI00907 Enhances Antidepressant-Like Behavioral Effects of the SSRI Fluoxetine," *Neuropsychopharmacology* (2005) vol. 30, No. 12, pp. 2205-2215.
Marek, et al., "Synergistic action of 5-HT2A antagonists and selective serotonin reuptake inhibitors in neuropsychiatric disorders," *Neuropsychopharmacology* (2003) 28:402-412.
Matsumura et al., "A New Method for Synthesis of Unsymmetrical Ureas Using Electochemically Prepared Trifluoroethyl Carbamates," J. Org. Chem. 65:1549-1551 (2000).
Medical Review(s), Application No. 207318Orig1s000, Center for Drug Evaluation and Research, Submission Date Sep. 1, 2015 [available online Jun. 3, 2016]. Retrieved from the Internet (URL): <https://www.accessdata.fda.gov/drugsatfda_docs/nda/2016/207318Oriq1s000MedR.pdf> (173 pages).

Meltzer et al., "Co-therapy with pimavanserin and risperidone 2 mg provides an improved clinical profile," *Schizophrenia Research* (2008) vol. 98, pp. 16.
Meltzer et al., "Pimavanserin, a Serotonin(2A) Receptor Inverse Agonist, for the Treatment of Parkinson's Disease Psychosis," *Neuropsychopharmacology* (2010) vol. 35, No. 4, pp. 881-892.
Meltzer et al., "Serotonin Receptors: Their Key Role in Drugs to Treat Schizophrenia," *Progress in Neuro-Pyschopharmacology & Biol. Psych.* (2003) vol. 27, pp. 1159-1172.
Meltzer, et al., "Plasma clozapine levels and the treatment of L-DOPA-induced psychosis in Parkinson's disease," *Neuropsychopharmacology* (1995) 12(1):39-45.
Meltzer, H. Y. "The role of serotonin in antipsychotic drug action," *Neuropsychopharmacology* (1999) 21(2S): 106S-115S.
Morley et al., "Antibody to Amyloid p Protein Alleviates Imparied Acquisition, Retention, and Memory Processing in SAMP8 Mice," *Neurobiology of Learning and Memory* (2002), 78(1):125-138.
Naritomi et al., "Prediction of human hepatic clearance from in vivo animal experiments and in vitro metabolic studies with liver microsomes from animals and humans," *Drug Metab. Dispos.* (2001) vol. 29, No. 10, pp. 1316-1324.
NDA Approval/Supplement Approval, NDA 210793 NDA 207318/S-003, Letter Signed Jun. 28, 2018. Retrieved from the Internet (URL): https://www.accessdata.fda.gov/drugsatfda_docs/appletter/2018/210793Orig1s000,207318Orig1s003ltr.pdf (5 pages).
Nebigil et al., "Serotonin is a novel survival factor of cardiomyocytes: mitochondria as a tarqet of 5-HT2B-receptor signaling," *FASEB J.* (2003) vol. 27, No. 10, pp. 1373-1375.
Ng, et al., "L-dopa-induced release of cerebral monoamines," *Science* (1970) 170:76-77.
Nordstrom, et al., "High 5-HT2 receptor occupancy in clozapine treated patients demonstrated by PET," *Psychopharmacology* (1993) 110:365-367.
Norton et al., "Caregivers of PDP patients have an increased risk of developing emotional and social distress that is decreased when PDP is treated with pimavanserin," (Meeting Abstract) *Journal of Parkinson's Disease* (Sep. 2016) vol. 6, No. S1, pp. 257, Abstract No. P42.11.
Norton et al., "Decreased burden among caregivers of patients with Parkinson's disease psychosis (PDP) treated with pimavanserin, a selective 5-HT2A inverse agonist," (Meeting Abstract) *Journal of Parkinson's Disease* (Sep. 2016) vol. 6, No. S1, p. 88, Abstract No. P12.08.
Obach et al., "The Prediction of Human Pharmacokinetic Parameters from Preclinical and In Vitro Metabolism Data," *J. Pharm. Exp. Therap.* (1997) vol. 283, No. 1, pp. 46-58.
Ogawa, et al., "Effects of R-102444 and its active metabolite R-96544, selective 5-HT2A receptor antagonists, on experimental acute and chronic pancreatitis: Additional evidence for possible involvement of 5-HT2A receptors in the development of experimental pancreatitis," *European Journal of Pharmacology* (2005) 521:156-163.
Paiva, et al., "Effects of ritanserin on sleep disturbances of dysthymic patients," *Psychopharmacology* (1988) 96:395-399.
Patel, et al., "The highly selective 5-hydroxytryptamine (5-HT)2A receptor antagonist, EMO 281014, significantly increases swimming and decreases immobility in male congenital learned helpless rats in the forced swim test," *Synapse* (2004) 52:73-75.
Pierce, et al., "5-hydroxytryptamine-induced synovial plasma extravasation is mediated via 5-hydroxytryptamine2A receptors on sympathetic efferent terminals," *The Journal of Pharmacology and Experimental Therapeutics* (1995) 275(1):502-508.
Poewe, W. "Psychosis in Parkinson's disease," *Movement Disorders* (2006) vol. 18, Suppl. 6, pp. S80-S87.
Pollak, et al., "Clozapine in drug-induced psychosis in Parkinson's disease," *Lancet* (1999) 353:2041-2042.
Price et al., "Pimavanserin, a 5-HT2A receptor inverse agonist, reverses psychosis-like behaviors in a rodent model of Alzheimer's disease," *Behavioural Pharmacology* (2002), 23:426-433.
R&D Focus Drug News (Jan. 24, 2000). Pimvaserin ACADIA lead compounds identified.
R&D Focus Drug News (Nov. 12, 2001). Pimvaserin ACADIA preclinical data.

(56) References Cited

OTHER PUBLICATIONS

Sadzot, et al., "Hallucinogenic drug interactions at human brain 5-HT2 receptors: Implications for treating LSD-induced hallucinogenesis," *Psychopharmacology* (1989) 98:495-499.
Saltzman, et al., "Cloning of the human serotonin 5-HT2 and 5-HT1C receptor subtypes," *Biochemical and Biophysical Research Communications* (1991) 181(3):1469-1478.
Sandler and Karo, Chapter E., "Reaction of Amines with Urethanes and Carbamates," Organic Functional Group Preparations, Academic Press pp. 161-162 (1986).
Satori and Maggi, "Acyclic and Cyclic Ureas," Science of Synthesis 18: 695-699 (2005).
Saxena, et al., "Cardiovascular effects of serotonin agonists and antagonists," *Journal of Cardiovascular Pharmacology* (1990) 15(Supp. 7):S17-S34.
Shanmugam, S. "Granulation Techniques and Technologies: Recent Progresses," *BioImpacts* (2015) vol. 5, No. 1, pp. 55-63.
Shigemori et al., "The factoral structure of the mini mental state examination (MMSE) in Japanese dementia patients," BMC Geriatrics 10(36): 7 pages (2010).
Stoner et al., "Integrated oral bioavailability projection using in vitro screening data as a selection tool in drug discovery," *Int. J. Pharm.* (2004) vol. 269, No. 1, pp. 241-249.
Swedish Search Report for Patent Application No. 1730232-4 dated Mar. 28, 2018 (10 pages).
Thavonekham, "A Practical Synthesis of Ureas from Phenyl Carbamates," Synthesis 11:1189-1194 (1997).
Vanover et al., "Pharmacological Characterization of AC-90179 [2-(4-Methoxy-phenyl)-N-(4-methyl-benzyl)-N-(1-methyl-piperidin-4-yl)-acetamide Hydrochloride]: A Selective Serotonin 2A Receptor Inverse Agonist," *J. Pharmacology & Experimental Therapeutics* (2004) vol. 310, No. 3, pp. 943-951.
Vanover, Kimberly E. et al., "Pharmacokinetics, tolerability, and safety of ACP-103 following single or multiple oral dose administration in healthy volunteers," *Journal of Clinical Phamacol.* (2007) vol. 47, No. 6, pp. 704-714.
Vanover, Kimberly E. et al., "Pharmacological and Behavioral Profile of N-(4-Fluorophenylmethyl)-N-(1-methylpiperidin-4-yl)-N'-(4-(2-methylpropyloxy)phenylmethyl) Carbamide (2R,3R)-Dihydroxybutanedioate (2:1) (ACP-103), a Novel 5-Hydroxytryptamine$_{2A}$ Receptor Inverse Agonist," *The Journal of Pharmacology and Experimental Therapeutics* (2006) 317(2):910-918.
Vinogradova et al., Palladium Catalyzed Cross-Coupling of Aryl Chlorides and Triflates with Socium Cyanate: A Practical Synthesis of Unsymmetrical Ureas, J. Am. Chem. Soc. 134:11132-11135 (2012).
Volk et al., "Synthesis of methyl ethyl and phenyl 4 2 methylpropoxy benzyl carbamates," The IP.com Prior Art Database, Disclosure No. IPCOM000244271D, (Nov. 27, 2015).
Weintraub et al., "Association of Dopamine Agonist Use With Impulse Control Disorders in Parkinson Disease," *Arch Neurol.* 2006 63(7):969-973.
Weintraub et al., "Clinical Spectrum of Impulse Control Disorders in Parkinson's Disease," *Movement Disorders* 2015 30(2):121-127.
Wood et al., "The Use of the Neuropsychiatric Inventory in Nursing Home Residents: Characterization and Measurement," Am. J. Geriatr. Psychiatr. 8(1):75-83 (2000).
Ye et al. "Improving response inhibition in Parkinson's disease with Atomoxetine." Biological Psychiatry, Apr. 15, 2015, 77, 740-748.
Yoshimura et al., "Hypervalent Iodine Catalyzed Hofmann Rearrangement of Carboxamides Using Oxone as Terminal Oxidant," JOC 77:11399-11404 (2012).
Yoshimura et al., (Tosylimino)phenyl-λ3-iodane as a Reagent for the Synthesis of Metyl Carbamates via Hofmann Rearrangement of Aromatic and Aliphatic Carboxamides, Journal of Organic Chemistry 77:2087-2091 (2012).

*Acadia Pharmaceuticals Inc.* v. *Aurobindo Pharma Ltd., et al.* Civil Action No. 1:20-cv-00985-RGA, Declaration of R. Christian Moreton, Ph.D.in Support of Defendants' Reply Claim Construction Brief, dated Jan. 19, 2022 (11 pages).
*Acadia Pharmaceuticals Inc.* v. *Aurobindo Pharma Ltd., et al.* Civil Action No. 1:20-cv-00985-RGA, Defendants' Sur-Reply Claim Construction Brief, dated Jan. 21, 2022 (23 pages).
*Acadia Pharmaceuticals Inc.* v. *Aurobindo Pharma Ltd., et al.* Civil Action No. 1:20-cv-00985-RGA, Acadia's Opening Claim Construction Brief, dated Oct. 8, 2021 (24 pages).
Acadia's NUPLAZID® product information, Retrieved from the Internet (URL): https://www.acadia-pharm.com/product/ (dated Oct. 4, 2021, 2 pages) (Exhibit 1 of *Acadia Pharmaceuticals Inc.* v. *Aurobindo Pharma Ltd., et al.* Civil Action No. 1:20-cv-00985-RGA, Acadia's Opening Claim Construction Brief, dated Oct. 8, 2021).
Highlights of Prescribing Information NUPLAZID™ (pimavanserin), Revised Apr. 2016. Retrieved from the Internet (URL): https://www.accessdata.fda.gov/drugsatfda_docs/label/2016/207318lbl.pdf (14 pages) (Exhibit 2 of *Acadia Pharmaceuticals Inc.* v. *Aurobindo Pharma Ltd., et al.* Civil Action No. 1:20-cv-00985-RGA, Acadia's Opening Claim Construction Brief, dated Oct. 8, 2021).
Highlights of Prescribing Information NUPLAZID® (pimavanserin), Revised Jun. 2018. Retrieved from the Internet (URL): https://www.accessdata.fda.gov/drugsatfda_docs/label/2018/207318s005lbl.pdf (15 pages) (Exhibit 3 of *Acadia Pharmaceuticals Inc.* v. *Aurobindo Pharma Ltd., et al.* Civil Action No. 1:20-cv-00985-RGA, Acadia's Opening Claim Construction Brief, dated Oct. 8, 2021).
2017 U.S. Pharmacopeia National Formulary, vol. 1 (7 pages) (Exhibit 4 of *Acadia Pharmaceuticals Inc.* v. *Aurobindo Pharma Ltd., et al.* Civil Action No. 1:20-cv-00985-RGA, Acadia's Opening Claim Construction Brief, dated Oct. 8, 2021).
*Acadia Pharmaceuticals Inc.* v. *Aurobindo Pharma Ltd., et al.* Civil Action No. 1:20-cv-00985-RGA, Declaration of R. Christian Moreton, Ph.D in Support of Defendants' Answering Claim Construction Brief, dated Nov. 12, 2021 (28 pages).
*Acadia Pharmaceuticals Inc.* v. *Aurobindo Pharma Ltd., et al.* Civil Action No. 1:20-cv-00985-RGA, Declaration of R. Christian Moreton, Ph.D in Support of Defendants' Answering Claim Construction Brief, dated Nov. 12, 2021 (64 pages).
*Acadia Pharmaceuticals Inc.* v. *Aurobindo Pharma Ltd., et al.* Civil Action No. 1:20-cv-00985-RGA, Defendants' Responsive Claim Construction Brief, dated Nov. 12, 2021 (30 pages).
USP 40 Phase-solubility analysis-general information, Retrieved from the Internet (URL): www.getintopharma.com <http://www.getintopharma.com> (5 pages) (Exhibit 1 of *Acadia Pharmaceuticals Inc.* v. *Aurobindo Pharma Ltd., et al.* Civil Action No. 1:20-cv-00985-RGA, Declaration of R. Christian Moreton, Ph.D in Support of Defendants' Answering Claim Construction Brief, dated Nov. 12, 2021).
Curriculum Vitae of Richard Christian Moreton (29 pages) (Exhibit A of *Acadia Pharmaceuticals Inc.* v. *Aurobindo Pharma Ltd., et al.* Civil Action No. 1:20-cv-00985-RGA, Declaration of R. Christian Moreton, Ph.D in Support of Defendants' Answering Claim Construction Brief, dated Nov. 12, 2021).
*Acadia Pharmaceuticals Inc.* v. *Aurobindo Pharma Ltd., et al.* Civil Action No. 1:20-cv-00985-RGA, Acadia's Reply Claim Construction Brief, dated Dec. 17, 2021 (28 pages).
*Acadia Pharmaceuticals Inc.* v. *Aurobindo Pharma Ltd., et al.* Civil Action No. 1:20-cv-00985-RGA, Declaration of Alexander M. Klibanov, Ph.D., in Support of Plaintiff's Reply Claim Construction Brief, dated Dec. 16, 2021 (61 pages).
Curriculum vitae of Alexander M. Klibanov (43 pages) (Exhibit A of *Acadia Pharmaceuticals Inc.* v. *Aurobindo Pharma Ltd., et al.* Civil Action No. 1:20-cv-00985-RGA, Declaration of Alexander M. Klibanov, Ph.D., in Support of Plaintiff's Reply Claim Construction Brief, dated Dec. 16, 2021).
Notice Letter of Paragraph IV Certification Regarding U.S. Pat. Nos. 10,449,185 and 10,646,480 from Aurobindo Pharma Ltd. to Acadia Pharmaceuticals, Inc. dated Jun. 10, 2020 (179 pages).
Notice Letter of Paragraph IV Certification Regarding U.S. Pat. No. 10,449,185 from Teva Pharmaceuticals USA, Inc. to Acadia Pharmaceuticals, Inc. dated Jun. 10, 2020 (83 pages).

(56) References Cited

OTHER PUBLICATIONS

Notice Letter of Paragraph IV Certification Regarding U.S. Pat. Nos. 7,732,615; 7,923,564; and 10,449,185 from MSN Laboratories Private Ltd. to Acadia Pharmaceuticals, Inc. dated Jun. 15, 2020 (18 pages).
Notice Letter of Paragraph IV Certification Regarding U.S. Pat. No. 10,646,480 from MSN Laboratories Private Ltd. to Acadia Pharmaceuticals, Inc. dated Jun. 18, 2020 (28 pages).
Notice Letter of Paragraph IV Certification Regarding U.S. Pat. Nos. 10,449,185, and 10,646,480 from Zydus Pharmaceuticals (USA) Inc. to Acadia Pharmaceuticals, Inc. dated Jun. 22, 2020 (67 pages).
Notice Letter of Paragraph IV Certification Regarding U.S. Pat. No. 10,646,480 from Teva Pharmaceuticals USA, Inc. to Acadia Pharmaceuticals, Inc. dated Jun. 23, 2020 (18 pages).
Notice Letter of Paragraph IV Certification Regarding U.S. Pat. No. 10,849,891 from Teva Pharmaceuticals USA, Inc. to Acadia Pharmaceuticals, Inc. received Dec. 23, 2020 (16 pages).
Notice Letter of Paragraph IV Certification Regarding U.S. Pat. No. 10,849,891 from Aurobindo Pharma Ltd. to Acadia Pharmaceuticals, Inc. dated Jan. 13, 2021 (26 pages).
Notice Letter of Paragraph IV Certification Regarding U.S. Pat. No. 10,849,891 from Zydus Pharmaceuticals (USA) Inc. to Acadia Pharmaceuticals, Inc. received Feb. 17, 2021 (22 pages).
Notice Letter of Paragraph IV Certification Regarding U.S. Pat. No. 10,849,891 from MSN Laboratories Private Ltd. to Acadia Pharmaceuticals, Inc. received Apr. 16, 2021 (38 pages).
*Acadia Pharmaceuticals Inc. v. Aurobindo Pharma Ltd., et al.* Civil Action No. 1:20-cv-00985-RGA, Defendants' Initial Invalidity Contentions, dated Apr. 26, 2021 (241 pages) (redacted).
*Acadia Pharmaceuticals Inc. v. Aurobindo Pharma Ltd., et al.* Civil Action No. 1:20-cv-00985-RGA, Joint Claim Construction Brief, filed Jan. 28, 2022 (93 pages).
*Acadia Pharmaceuticals Inc. v. Aurobindo Pharma Ltd., et al.* Civil Action No. 1:20-cv-00985-RGA, Joint Claim Construction Appendix, filed Jan. 28, 2022 (225 pages).
*Acadia Pharmaceuticals Inc. v. Aurobindo Pharma Ltd., et al.* Civil Action No. 20-985-RGA, Memorandum Opinion, filed Apr. 6, 2022 (13 pages).
*Acadia Pharmaceuticals Inc. v. Aurobindo Pharma Limited and Aurobindo Pharma USA, Inc.*, D.Del. Civil Action No. 1-20-cv-00985: Complaint against Aurobindo Pharma Limited and Aurobindo Pharma USA, Inc. filed by Acadia Pharmaceuticals Inc., Jul. 24, 2020 (127 pages).
*Acadia Pharmaceuticals Inc. v. Hetero Labs Limited, Hetero Labs Limited Unit-V, and Hetero USA Inc.*, D.Del. Civil Action No. 1-20-cv-01022: Complaint against Hetero Labs Limited, Hetero Labs Limited Unit-V, and Hetero USA Inc. filed by Acadia Pharmaceuticals Inc., Jul. 30, 2020 (90 pages).
*Acadia Pharmaceuticals Inc. v. MSN Laboratories Private Ltd. and MSN Pharmaceuticals, Inc.*, D.Del. Civil Action No. 1-20-cv-01029: Complaint against MSN Laboratories Private Ltd. and MSN Pharmaceuticals, Inc. filed by Acadia Pharmaceuticals Inc., Jul. 30, 2020 (71 pages).
*Acadia Pharmaceuticals Inc. v. Teva Pharmaceuticals USA, Inc. and Teva Pharmaceutical Industries Ltd.*, D.Del. Civil Action No. 1-20-cv-00986: Complaint against Teva Pharmaceuticals USA, Inc. and Teva Pharmaceutical Industries Ltd. filed by Acadia Pharmaceuticals Inc., Jul. 24, 2020 (126 pages).
*Acadia Pharmaceuticals Inc. v. Zydus Pharmaceuticals (USA) Inc. and Cadila Healthcare Limited*, D.Del. Civil Action No. 1-20-cv-01021: Complaint against Zydus Pharmaceuticals (USA) Inc. and Cadila Healthcare Limited filed by Acadia Pharmaceuticals Inc., Jul. 30, 2020 (153 pages).

\* cited by examiner

| EMPTY HARD CAPSULE SPECIFICATIONS | | | | | | | |
|---|---|---|---|---|---|---|---|
| APPROXIMATE COMPARATIVE SIZE | CAPSULE SIZE | CONVENTIONAL FILL WEIGHT (mg) | | | VOLUME (Theoretical) (ml) | LENGTH ±0.8(mm) | EXTERNAL DIAMETER (mm) | WEIGHT ±10% |
| | | TYPICAL POWDER DENSITY | | | | | | |
| | | 0.45 (light) | 0.7 (standard) | 1.0 (heavy) | | | | |
| | 000 | 615 | 960 | 1370 | 1.37 | 26.1 | 9.9 | 163 |
| | 00 | 430 | 665 | 950 | 0.95 | 23.3 | 8.5 | 118 |
| | 0 | 305 | 475 | 680 | 0.68 | 21.7 | 7.65 | 96 |
| | 1 | 225 | 350 | 500 | 0.5 | 19.4 | 6.91 | 76 |
| | 2 | 165 | 260 | 370 | 0.37 | 18.0 | 6.35 | 61 |
| | 3 | 135 | 210 | 300 | 0.3 | 15.9 | 5.82 | 48 |
| | 4 | 95 | 145 | 210 | 0.21 | 14.3 | 5.31 | 38 |
| | 5 | 60 | 90 | 130 | 0.13 | 11.1 | 4.91 | 28 |

FIG. 1

FORMULATIONS OF PIMAVANSERIN

CROSS-REFERENCE TO RELATED APPLICATIONS

This application is a continuation of U.S. patent application Ser. No. 17/080,731, filed on Oct. 26, 2020, which is a continuation of U.S. patent application Ser. No. 16/836,086, filed on Mar. 31, 2020, which is a continuation of U.S. patent application Ser. No. 16/571,554, filed on Sep. 16, 2019, which is a continuation of U.S. patent application Ser. No. 16/363,378, filed on Mar. 25, 2019, which is a continuation of International Patent Application No. PCT/US2018/048096, filed on Aug. 27, 2018, which claims priority to and the benefit of U.S. Provisional Patent Application No. 62/552,300, filed Aug. 30, 2017, and Swedish Patent Application No. 1730232-4, filed Sep. 1, 2017.

BACKGROUND

Pimavanserin, the active component in Nuplazid®, is approved for treatment of hallucinations and delusions associated with Parkinson's disease psychosis at a dose of 34 mg, taken as two 17 mg tablets once a day. The tablets are immediate release, film-coated tablet containing 20 mg of pimavanserin tartrate, which is equivalent to 17 mg of pimavanserin free base. Inactive ingredients include pregelatinized starch, magnesium stearate, and microcrystalline cellulose. Additionally, the following inactive ingredients are present as components of the film coat: hypromellose, talc, titanium dioxide, polyethylene glycol, and saccharin sodium.

Patients suffering from neurodegenerative diseases, such as Parkinson's disease are at a risk of non-compliance when administered a drug of too large size, or if taken as more than one tablet per day as said patients often have difficulty swallowing. Formulations of pimavanserin are described in WO 2007/133802. Pimavanserin is currently approved and administered as tablets containing 20 mg pimavanserin tartrate (equivalent to 17 mg pimavanserin), taken as two tablets once a day. Each with a total 150 mg tablet weight before film coating, i.e. total weight per dose is 300 mg (equivalent to 34 mg pimavanserin). In order to simplify administration and patient compliance of pimavanserin it would be advantageous to administer pimavanserin as a single dose.

Improved manufacturing processes for single unit dose forms, particularly for smaller sized single unit dosage forms, for oral administration of a therapeutic quantity of pimavanserin are critical. The physical properties of pimavanserin, e.g. bulk density and flow, when prepared in a tablet form requires, e.g. binders and other agents that increase the finished dosage size. Pimavanserin manufactured following conventional techniques has low bulk density and poor flowability and a tendency to clump, which will adversely impact reproducibility and quantitative accurate filling of capsules during the manufacturing process.

Consequently there is a need to improve the properties of pimavanserin allowing dosing of the daily therapeutic dose as a single administration.

SUMMARY

Provided herein are capsules comprising 5-34 mg pimavanserin (equivalent to 6-40 mg pimavanserin tartrate), or a pharmaceutically acceptable salt thereof Provided herein are also pharmaceutical compositions consisting of 5-34 mg pimavanserin or a pharmaceutically acceptable salt thereof, a filler and a lubricant.

Provided herein are also processes for manufacturing a capsule comprising 5-34 mg pimavanserin or a pharmaceutically acceptable salt thereof comprising: adding water to pimavanserin or a pharmaceutically acceptable salt thereof, and granulating pimavanserin or a pharmaceutically acceptable salt thereof with the water; controlling the impeller speed and/or amperage; drying the granulated pimavanserin or a pharmaceutically acceptable salt thereof; sizing the dried granulated pimavanserin or a pharmaceutically acceptable salt thereof; blending the dried and granulated pimavanserin or a pharmaceutically acceptable salt thereof and one or more filler; encapsulating the blended pimavanserin composition in a capsule of size 3 or 4.

BRIEF DESCRIPTION OF THE DRAWINGS

FIG. 1 shows a table disclosing specifications of capsule sizes, commercially available.

DETAILED DESCRIPTION

Definitions

Figure 2:
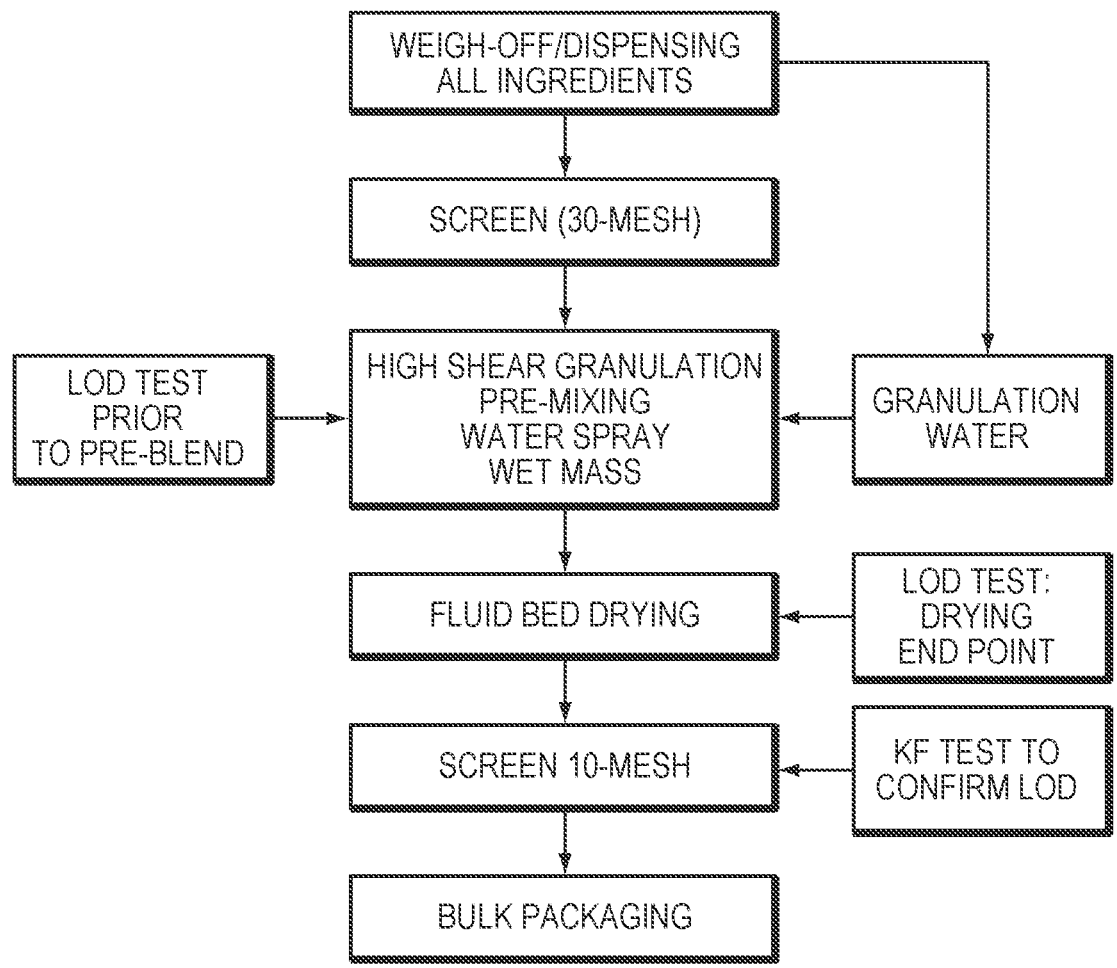
FIG. 2 schematically discloses a process flow chart for pimavanserin granulation.
Figure 3:
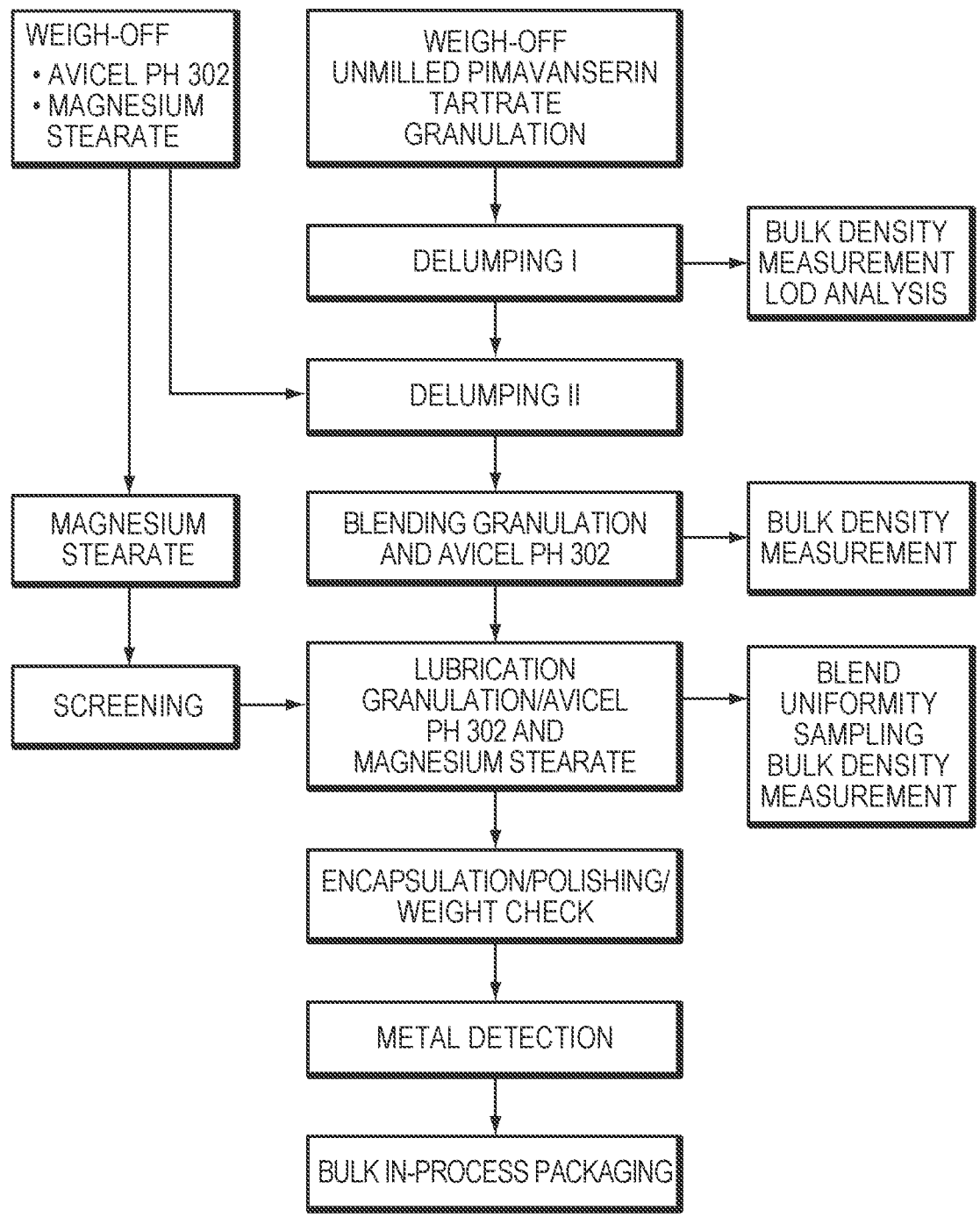
FIG. 3 schematically discloses a process flow chart for encapsulating pimavanserin granulation

Unless defined otherwise, all technical and scientific terms used herein have the same meaning as is commonly understood by one of ordinary skill in the art. All patents, applications, published applications and other publications referenced herein are incorporated by reference in their entirety. In the event that there are a plurality of definitions for a term herein, those in this section prevail unless stated otherwise.

As used herein, "pharmaceutical composition" refers to a composition of one or more active pharmaceutical ingredient(s) alone, or administered with other chemical components, such as diluents, binders, lubricants, pharmaceutical flow agents, and/or other excipients, e.g. for forming a unit dose, such as a tablet, a capsule etc.

As used herein, "physiologically acceptable" defines a diluent, binder, or excipient that does not abrogate the biological activity and properties of the pharmaceutically active compound.

As used herein, "pharmaceutically acceptable salt" refers to a salt of a compound that does not abrogate the biological activity and properties of the compound. Pharmaceutical salts can be obtained by reaction of a compound disclosed herein with an acid or base. Base-formed salts include, without limitation, ammonium salt ($NH_4^+$); alkali metal, such as, without limitation, sodium or potassium, salts; alkaline earth, such as, without limitation, calcium or magnesium, salts; salts of organic bases such as, without limitation, dicyclohexylamine, piperidine, piperazine, methylpiperazine, N-methyl-D-glucamine, diethylamine, ethylenediamine, tris(hydroxymethyl)methylamine; and salts with the amino group of amino acids such as, without limitation, arginine and lysine. Useful acid-based salts include, without limitation, acetates, adipates, aspartates, ascorbates, benzoates, butyrates, caparate, caproate, caprylate, camsylates, citrates, decanoates, formates, fumarates, gluconates, glutarate, glycolates, hexanoates, laurates, lactates, maleates, nitrates, oleates, oxalates, octanoates, propanoates, palmitates, phosphates, sebacates, succinates, stearates, sulfates, sulfonates, such as methanesulfonates, ethanesulfonates, p-toluenesulfonates, salicylates, tartrates, and tosylates.

Pharmaceutically acceptable solvates and hydrates are complexes of a compound with one or more solvent of water molecules, or 0.5 to about 100, or 1 to about 100, or 1 to about 10, or one to about 2, 3 or 4, solvent or water molecules.

As used herein, to "modulate" the activity of a receptor means either to activate it, i.e., to increase its cellular function over the base level measured in the particular environment in which it is found, or deactivate it, i.e., decrease its cellular function to less than the measured base level in the environment in which it is found and/or render it unable to perform its cellular function at all, even in the presence of a natural binding partner. A natural binding partner is an endogenous molecule that is an agonist for the receptor.

An "agonist" is defined as a compound that increases the basal activity of a receptor (e.g. signal transduction mediated by the receptor).

As used herein, "partial agonist" refers to a compound that has an affinity for a receptor but, unlike an agonist, when bound to the receptor it elicits only a fractional degree of the pharmacological response normally associated with the receptor even if a large number of receptors are occupied by the compound.

An "inverse agonist" is defined as a compound, which reduces, or suppresses the basal activity of a receptor, such that the compound is not technically an antagonist but, rather, is an agonist with negative intrinsic activity.

As used herein, "antagonist" refers to a compound that binds to a receptor to form a complex that does not give rise to any response, as if the receptor was unoccupied. An antagonist attenuates the action of an agonist on a receptor. An antagonist may bind reversibly or irreversibly, effectively eliminating the activity of the receptor permanently or at least until the antagonist is metabolized or dissociates or is otherwise removed by a physical or biological process.

As used herein, a "subject" refers to an animal that is the object of treatment, observation or experiment. "Animal" includes cold- and warm-blooded vertebrates and invertebrates such as birds, fish, shellfish, reptiles and, in particular, mammals. "Mammal" includes, without limitation, mice; rats; rabbits; guinea pigs; dogs; cats; sheep; goats; cows; horses; primates, such as monkeys, chimpanzees, and apes, and, in particular, humans.

As used herein, an "excipient" refers to an inactive ingredient that is added to a pharmaceutical composition to provide, without limitation, bulk, consistency, stability, binding ability, lubrication, disintegrating ability, etc., to the composition. A "diluent" is a type of excipient.

As used herein, a "diluent", "bulking agent" and "filler" refer to an ingredient (excipient) in a pharmaceutical composition that lacks pharmacological activity but may be pharmaceutically necessary or desirable, e.g. to enhance or improve the properties of the pharmaceutical blend for manufacturing or physiological purposes. For example, a diluent or filler may be used to increase the bulk of a potent drug whose mass is too small for manufacture or administration.

As used herein, a "binder" is an excipient holding the ingredients together, and forming granules or tablets with required mechanical strength, and may give volume to the formulation. Specific examples of binders are mono-, di-, and poly-saccharides and derivatives thereof; sugar alcohols such as xylitol, sorbitol or maltitol; protein, such as; synthetic polymers, such as polyvinylpyrrolidone (PVP), polyethylene glycol (PEG). Binders are classified according to their application, e.g. solution binders are dissolved in a solvent (for example water or alcohol may be used in wet granulation processes). Examples include gelatin, cellulose, cellulose derivatives, polyvinylpyrrolidone, starch, sucrose and polyethylene glycol. Dry binders are added to the powder blend, either after a wet granulation step, or as part of a direct powder compression (DC) formula. Examples include cellulose, methyl cellulose, polyvinylpyrrolidone and polyethylene glycol.

As used herein a "lubricant" refers to an excipient which for example prevents ingredients and excipients to lump together, and/or sticking to the capsule filling machine. A lubricant may also ensure that the formation, filing and ejection of the capsule can occur, for example by lowering friction. Examples of lubricants are talc, silicon dioxide (silica), fatty acids or fatty acid salts, such as magnesium stearate, sodium stearate fumarate, stearic acid, etc.

As used herein a "disintegrant" refers to an excipient which disintegrate a pharmaceutical preparation on contact with an aqueous fluid.

As used herein, "coadministration" of pharmacologically active compounds refers to the delivery of two or more separate chemical entities, whether in vitro or in vivo. Coadministration means the simultaneous delivery of separate agents; the simultaneous delivery of a mixture of agents; as well as the delivery of one agent followed by delivery of a second agent or additional agents. Agents that are coadministered are typically intended to work in conjunction with each other.

The term "an effective amount" as used herein means an amount of active compound or pharmaceutical agent that elicits the biological or medicinal response in a tissue, system, animal or human that is being sought by a researcher, veterinarian, medical doctor or other clinician, which includes alleviation or palliation of the symptoms of the disease being treated.

The terms screen, screening, delump, delumping, dry milling, and sizing are used interchangeably herein. These terms refer to separation according to size.

The term "granulation" as used herein, and as conventionally used in the pharmaceutical industry, refers to the act or process in which primary powder particles are made to adhere to form larger, multiparticle entities called granules. Granules may for example be formed collecting particles together by creating mechanical bonds between them, e.g. by compression or by using a binder. Granulation is extensively used in the manufacturing of tablets and capsules.

The terms "granulated pimavanserin" and "pimavanserin granulation" are used interchangeably herein.

Generally a granulation process combines one or more particles and forms a granule that will allow tableting or the encapsulation process to be within required limits. The granulation process can be made predictable and repeatable. The granulation can be performed in a variety of equipment such as, but not limited to, low shear, high shear granulators, fluid bed granulator, roller compactor, and slugger.

The term "blending" refers to the mixing of pharmaceutical ingredients to form a mixture of the ingredients, e.g. active pharmaceutical ingredient (API) and diluent, as defined by pharmaceutical specifications in the compendial references using a variety of equipment such as, but not limited to, "V"-blenders, bin-blenders, cone-blenders.

The term "encapsulation" refers to a range of techniques used to enclose medicines in a shell, e.g. a two-piece capsule, such as a two-piece hard shell capsule. The capsule referred to herein may be taken orally. Capsules may be designed with a telescoping cap and body manufactured from e.g. gelatin or cellulose.

Compounds

Pimavanserin, which is also known as N-(1-methylpiperidin-4-yl)-N-(4-fluorophenylmethyl)-N'-(4-(2-methylpropyloxy)phenylmethyl)carbamide, N-[(4-fluorophenyl)methyl]-N-(1-methyl-4-piperidinyl)-N'-[4-(2-methylpropoxy)phenyl]methyl -urea, 1-(4-fluorobenzyl)-1-(1-methylpiperidin-4-yl)-3-[4-(2-methylpropoxy)benzyl] urea, or ACP-103. Pimavanserin commonly is administered as pimavanserin tartrate and has the structure of Formula (I):

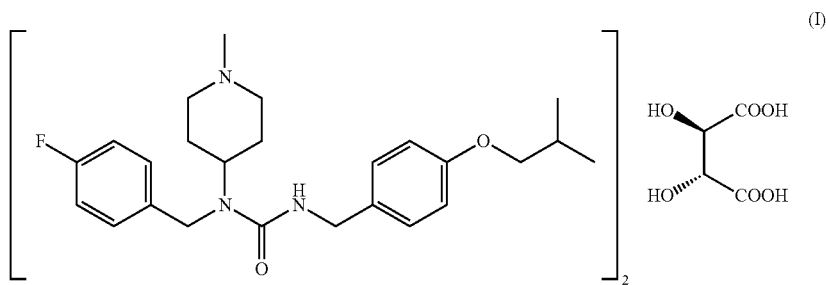

Pimavanserin has previously been synthesized according to the method disclosed in Scheme I.

SCHEME I: SYNTHESIS OF PIMAVANSERIN

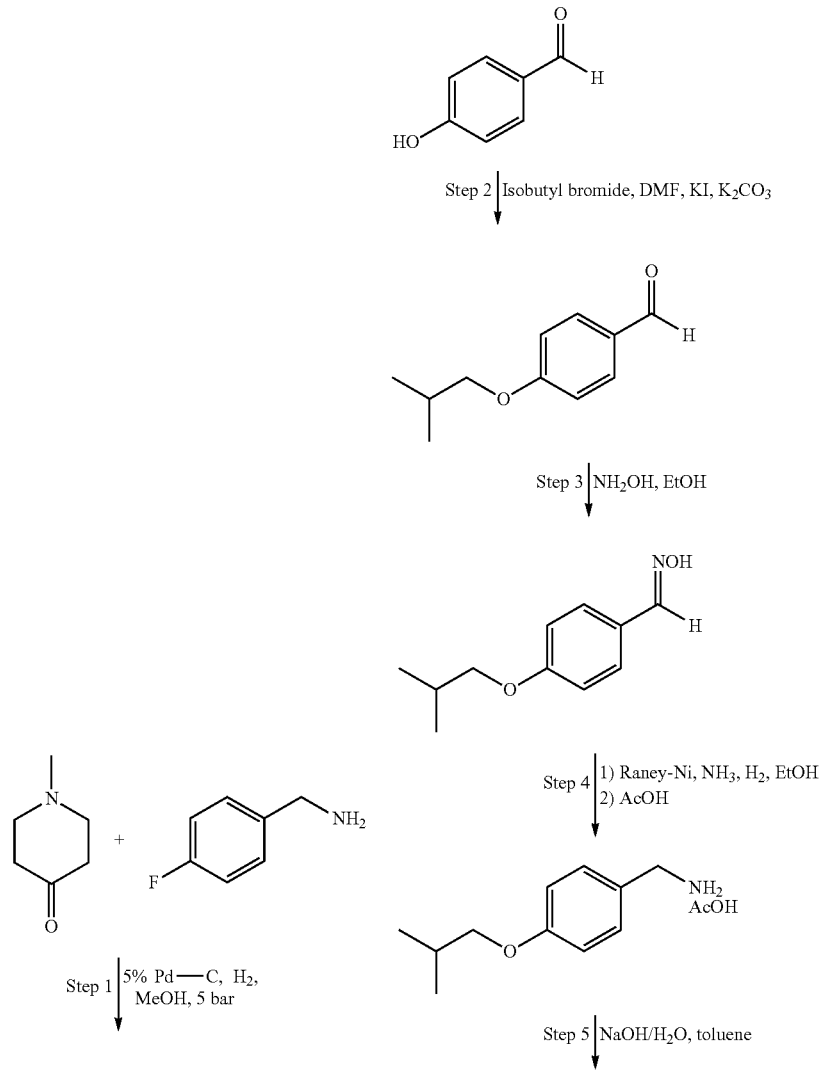

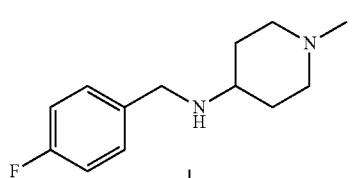
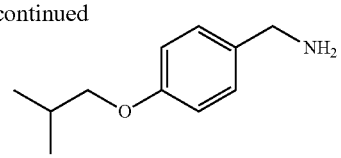

Step 6 | COCl₂, HCl, toluene

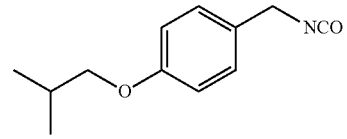

Step 7 | 1) THF
2) EtOH

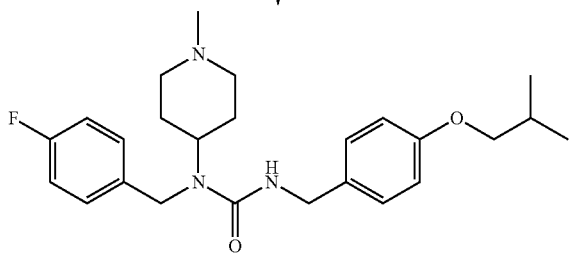

30

Alternative methods for preparing pimavanserin are disclosed in WO2017/015272, which is incorporated herein by reference in its entirety.

Pimavanserin and methods for its use are described in U.S. Pat. Nos. 7,601,740; 7,659,285; 7,713,995; 7,732,462; 7,994,193 and 8,008,323, the entirety of each of which is hereby incorporated by reference. Pimavanserin can be obtained in a number of salt and crystalline forms. Exemplary pharmaceutically acceptable salts include the tartrate, hemi-tartrate, citrate, fumarate, maleate, malate, phosphate, succinate, sulphate, and edisylate (ethanedisulfonate) salts. Pimavanserin salts including the aforementioned ions, among others, are described in U.S. Patent Publication No. 2006-0111399, filed Sep. 26, 2005, the entirety of which is incorporated herein by reference. In an embodiment provided herein, pimavanserin is the tartrate salt of pimavanserin. Several crystalline forms of the tartrate salt of pimavanserin have been described in U.S. Patent Publication No. 2006-0106063, filed Sep. 26, 2006, the entirety of which is incorporated herein by reference. See also U.S. Pat. Nos. 7,732,615; 7,795,547; 7,790,899; 7,868,176, the entirety of each of which is incorporated herein by reference. In an embodiment provided herein, pimavanserin is the crystalline form of the tartrate salt of pimavanserin Form A. In another embodiment, pimavanserin is the crystalline form of the tartrate salt of pimavanserin Form C. Pimavanserin (including, for example, the tartrate salt) may be formulated into tablets, such as is described in U.S. Patent Publication Nos. 2007-0260064, filed May 15, 2007 and 2007-0264330, filed May 15, 2007, each of which are incorporated herein by reference in their entireties.

The pharmacological activity of pimavanserin has been previously reported. See U.S. Patent Publication Nos. 2004/0213816 and 2009/0053329, the entirety of each of which is hereby incorporated by reference. Pimavanserin is active in a number of models thought to be predictive of antipsychotic activity such as DOI ((±)-2,5-dimethoxy-4-iodoamphetamine, a serotonin agonist) induced head twitches in the rat and attenuation of hyperactivity in mice induced by the N-methyl-D-aspartate antagonist MK-801. The compound was effective in these models at oral doses of 3 and 10 mg/kg.

Suitable routes of administration of pimanvanserin may, for example, include oral, rectal, transmucosal, topical, or intestinal administration; parenteral delivery, including intramuscular, subcutaneous, intravenous, intramedullary injections, as well as intrathecal, direct intraventricular, intraperitoneal, intranasal, or intraocular injections. The compounds can also be administered in sustained or controlled release dosage forms, including depot injections, osmotic pumps, pills, transdermal (including electrotransport) patches, and the like, for prolonged and/or timed, pulsed administration at a predetermined rate. Embodiments provided herein relate to oral administration of a capsule comprising pimavanserin granulation.

The pharmaceutical compositions described herein comprised in a capsule refer to compositions prepared by methodologies not conventionally used in granulation, such as high and low shear granulation, e.g. using low amounts of water.

For oral administration, the compositions can be formulated readily by combining the active pharmaceutical ingredient (API) (e.g., pimavanserin or pimavanserin tartrate) with pharmaceutically acceptable binders or diluents well known in the art. Such binders or diluents enable the API disclosed herein to be formulated as tablets, pills, dragees, capsules, liquids, gels, syrups, slurries, suspensions and the like, for oral ingestion by a patient to be treated.

Provided herein is pimavanserin and pharmaceutically acceptable salts thereof having altered properties, such as increased bulk density, improved flow, and compressibility allowing the pharmaceutical manufacturing of a capsule comprising about 5-34 mg pimavanserin, such as about 34 mg, which for example may be filled in a size 3 or 4 capsule, such as a capsule of size 4.

It has herein been demonstrated that altering the flow and bulk density of pimavanserin, and compositions comprising pimavanserin using methods described herein results in a reproducible and quantitatively accurate filling of small sized capsules (e.g. size 3 or 4 capsules) in a scaled up pharmaceutical manufacturing processes, e.g. for manufacturing of about 1,000,000 capsules or more, for example at a speed of 40-90,000 capsules per hour.

Pharmaceutical manufacturing as used herein implies certain requirement being met such as manufacturing efficiency and economical requirements. Although also product quality and performance are ensured through the design of effective and efficient manufacturing processes, product and process specifications are based on a mechanistic understanding of how formulation and process factors affect product performance, e.g. variability between batches, assuring continuous real-time quality of the product and the materials, e.g. excipients. Additionally, regulatory policies and procedures used to meet official requirements such as those set out by health authorities, such as EMA (European Medicine agency) and FDA (U.S. Food and Drug Administration) and similar agencies in order to obtain the required quality of a drug product has an impact on the pharmaceutical manufacturing. For example, risk-based regulatory approaches recognize the level of scientific understanding of how formulation and manufacturing process factors affect product quality and performance and the capability of process control strategies to prevent or mitigate the risk of producing a poor quality product. For example, manual filling of capsules would not be considered relevant by those skilled in the art as manual filling of capsules cannot provide high reproducibility at the filling speed required to manufacture batches containing more than 100,000 capsules. Consequently those skilled in the art setting out to improve the formulation of an existing active pharmaceutical ingredient (API) for example to improve patient compliance, are working with tools used within the field of pharmaceutical manufacturing of small molecules.

Generally when improving the flow of an API (active pharmaceutical ingredient) the fill weight is increased. Increasing the fill weight is counterproductive to filling a small volume, such as a size 3 or even a size 4 capsule, at the production speeds required, such as 40-90,000 capsules per hour.

Disclosed herein are pharmaceutical manufacturing processes for obtaining suitable strength capsules of pimavanserin or a pharmaceutically acceptable salt thereof, said process comprises spraying water to pimavanserin, followed by a granulation process, wherein pimavanserin is granulated without addition of a binder, and blending followed by encapsulation. The particle size distribution, and/or bulk density of the granulated pimavanserin is controlled and matched to other excipient(s) to improve flow of the composition and assure content uniformity and low variability of the product. Additionally matching of excipient(s) allows reproducibility during encapsulation of pimavanserin. The matching of physical properties of API and other excipients used herein enables pharmaceutical manufacturing, in particular capsule filling (encapsulating the dried pimavanserin granulation in capsules of size 3 or 4) at sufficient speed such as more than 40,000 capsules per hour. Matching of API may for example be done by matching the particle size distribution of the API and one or more excipient. The bulk density of the API and the one or more excipients may also be matched.

For example, as shown in table 1, pimavanserin granulation, as obtained by the pharmaceutical manufacturing described herein vs the native API (active pharmaceutical ingredient (e.g., pimavanserin tartrate), obtained for example as decribed in WO2017/015272), the bulk density and the Carr's Index (Carr's Compressibility Index) have been substantially altered which enables the filling of the above mentioned small capsule. Carr's Index compares the difference between the bulk density and tapped density of a substance to determine its compressibility. The bulk density and the Carr's Index may be determined in accordance with USP<616> (method for performing Bulk and Tapped Densities, method 1) and USP<1174> (definition of powder flow) respectively.

TABLE 1

|  | Pimavanserin granulation* | Native API |
| --- | --- | --- |
| Bulk density (g/ml) according to USP <616> | 0.508 (n = 4) | 0.294 (n = 2) |
| Carr's Index | 24 (n = 4) | 36 (n = 2) |

*final blend as disclosed in the example herein below and in table 2

Table 1 visualizes that filling of a capsule, in particular a capsule of size 3 or 4 (capsule volumes of 0.30 and 0.21 ml respectively, approximately 120 mg and 85 mg respectively at a bulk density of 0.5 g/ml). As evident from Table 1, native pimavanserin (API) would be challenging for a size 3 capsule and not possible for a capsule of size 4 without improving the bulk density (as comparison 85 mg of pimavanserin granulation would require about 0.17 ml compared to 0.29 ml for the native API) and flowability (Carr index is frequently used in pharmaceutical manufacturing as an indication of the flowability of a powder, e.g. 2016 U.S. Pharmacopoeias-National Formulary [USP 35 NF 30]).

In particular, disclosed herein are formulation, granulation, dry milling, blending, and encapsulation of pimavanserin containing novel elements. Salient features are that the known granulation technology uses atypical parameters to achieve the desired results. Spray rate, atomization and quantity of water are examples of atypical parameters used in combination with wet granulation to obtain the targeted properties of pimavanserin formulation disclosed herein. For example, pimavanserin has been successfully granulated without the use of binder by spraying, at a controlled rate and under controlled atomization conditions, a controlled amount of water to pimavanserin during the wet granulation to provide granulated pimavanserin suitable for further processing (e.g. drying, blending, etc.) in the pharmaceutical manufacturing of capsules containing 5-34 mg pimavanserin, such as 10-34 mg capsules of size 3 or 4. Prior to the surprising finding that pimavanserin could be successfully wet granulated achieving the targeted improved physical properties (e.g. bulk density) without the addition of a binder, and by adding a small, such as 2-15% w/w, e.g. 3-10% w/w, 3-8% w/w amount of water to pimavanserin by spraying, many different granulation methods were contemplated and tested, and some discussed more in detail hereinbelow.

In one embodiment, High Shear Granulation (HSG) utilizing a small quantity of water, such as approximately 3-8% w/w of the dry ingredients, under appropriate HSG parameters for atomization, spray rate, impeller speed, and chopper speed was found to provide the required improvements to the pimavanserin (API) physical properties, such as increased bulk density, improved flow, and compressibility. The small quantity of water, its application using appropriate water atomization and/or water application rate are important reasons for the improved properties of pimavanserin. It has herein been demonstrated that the atomized spraying of a small amount of water during the granulation of pimavanserin achieves a wetting of pimavanserin that provides a granulated pimavanserin suitable for pharmaceutical manufacturing of a capsule, such as a capsule of size 4 comprising 10-34 mg pimavanserin. The actual amount of water to be sprayed at the granulation of pimavanserin may vary from batch to batch (depending on surrounding factors such as humidity, temperature, exact properties of the API batch, etc) but is still consider to be a small amount, e.g. 3-10% w/w based on the dry ingredients. The amount of water and the granulation process disclosed herein is controlled by controlling the impeller energy to achieve the targeted impeller speed. The appropriate impeller speed ensures sufficient mixing and controls the growth of granules. The specific small amount of water needed for each batch is controlled by the power consumption (amperage) of the granulator, i.e., if the amperage is too high, additional amounts of water could be sprayed to the granulate in order to obtain pimavanserin having the properties desired in order to pharmaceutically manufacture capsules comprising 5-34 mg pimavanserin. Adding too much water may alter other properties of the API, such as its crystallinity. The properties are achieved via a manufacturing process that includes granulation, using a suitable granulator, e.g. a high shear granulator, simultaneously spraying the adequate amount of water while mixing, followed by screening, and blending appropriate quantities of excipients. In some embodiments the lack of a binder, and using pimavanserin, properly wetted and not over-wetted are believed to be reasons for the fill uniformity observed using the herein described manufacturing process. Over-wetted granulation could seriously affect the further processing. In some embodiments particle size distribution of the granulated pimavanserin is controlled and matched to the particle size distribution of the diluents and other excipients to minimize segregation and improve flow and capsule filling reproducibility. The particle size distribution is also considered a factor involved in the successful filing of capsules of size 3 or 4, as a too aggressive milling would cause a wider particle size distribution and hamper the encapsulation. Examples of suitable particles size distribution of the granulated pimavanserin is a particle size distribution (D90) of 60-450 µm, such as 100-420 µm, such as above 250 µm. Particle size distribution referred to herein is obtained using Laser light scattering particle size (LLS PS) analyses of granulated pimavanserin conducted on a Malvern Mastersizer 2000 LLS PS system using a Scirocco 2000 dry dispersion unit using standard non-GMP conditions, and in a sample size of about 2 -10 g. Suitable diluents such as microcrystalline cellulose, silicified microcrystalline cellulose, low substituted hydroxypropyl cellulose or similar materials to a concentration approximately one-half of the granulation and lubricated with magnesium stearate, sodium stearyl fumarate or other suitable lubricants to prevent sticking to the encapsulation tooling. In some embodiments the particle size distribution of the diluent is matched to the above mentioned particle size distribution of granulated pimavanserin, for example microcrystalline cellulose having a particle size distribution (D90) is 180-420 µm, such as above 250 µm. In some embodiments the lubricant, such as magnesium stearate is also matched to the API. In some embodiments the matching of the particle size distribution of the lubricant, compared to the diluent, is less important in view of the lower amounts used in some embodiments. Optionally suitable binders and/or disintegrants may be included in the blending of the pimavanserin granulation. In some embodiments pimavanserin is blended with a diluent, e.g. microcrystalline cellulose and lubricant, magnesium stearate only, whereas amounts of water were added by spraying during the granulation process In some embodiments the particle size distribution (D90) of the composition is 60-380 µm, such as 75-350 µm, such as 100-300 µm.

Figure 4:
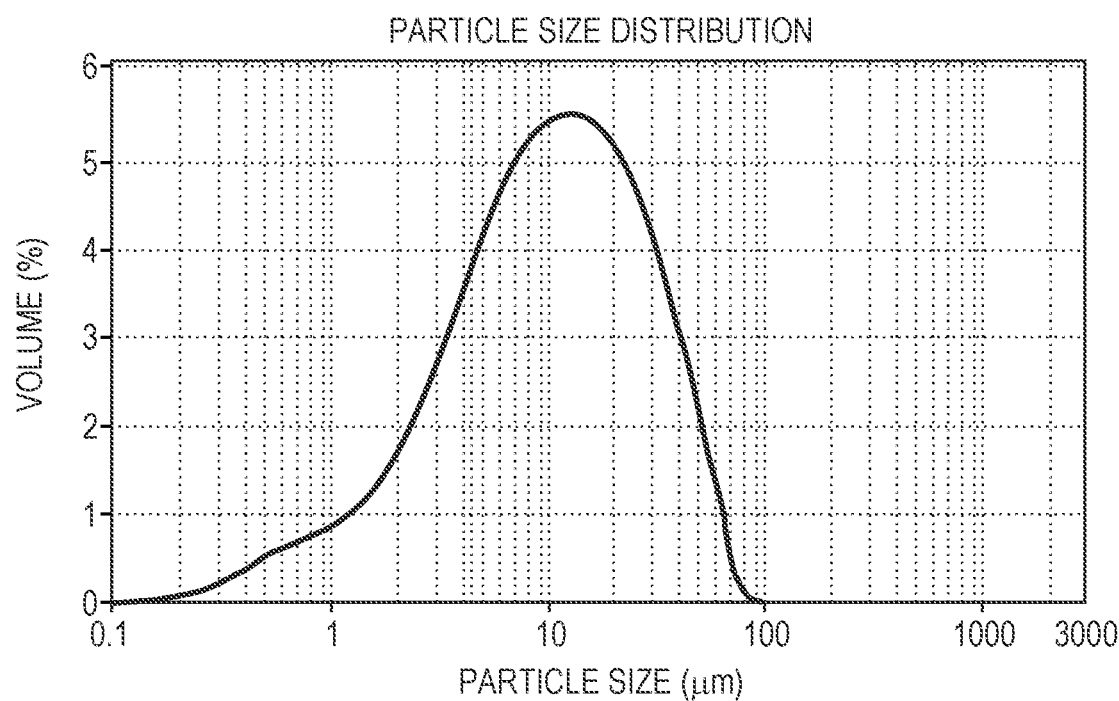
FIG. 4 shows a particle size distribution diagram of pimavanserin tartrate.

FIG. 4 discloses the particle size distribution of pimavanserin tartrate, prior to the herein disclosed granulation process.

Figure 5:
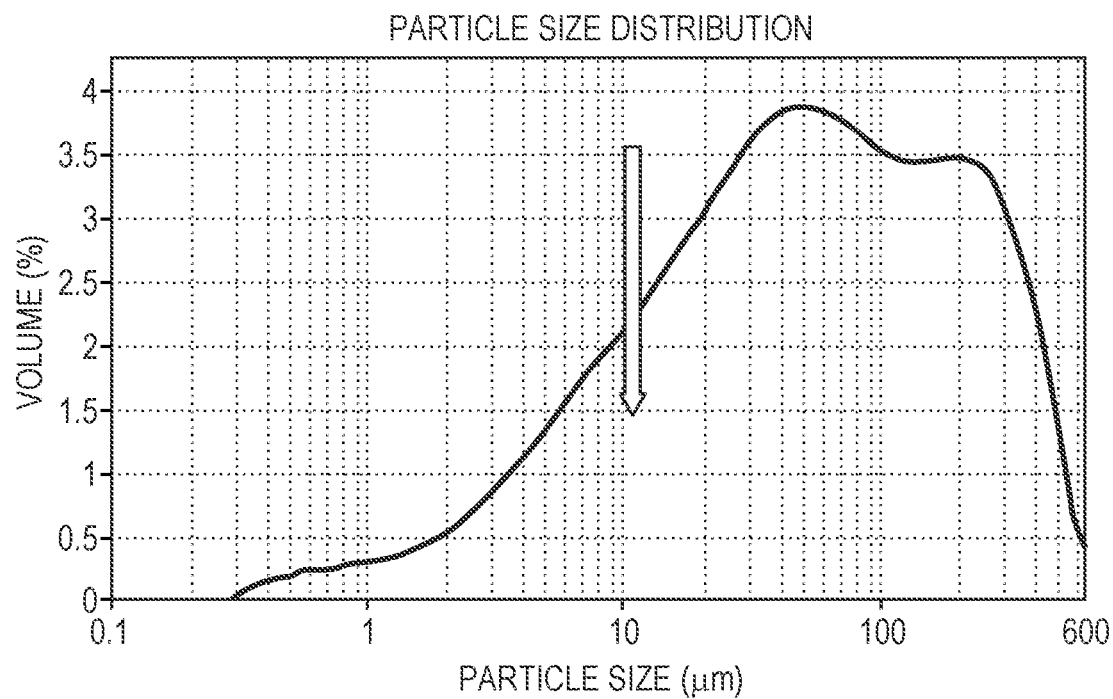
FIG. 5 shows a particle size distribution diagram of granulated pimavanserin.

FIG. 5 discloses the particle size distribution of the granulated pimavanserin. The arrow in FIG. 5 indicates the area of particles size distribution of the API. A substantial change in the particle size distribution can be seen, e.g. the D90 has increased from about 30 µm for the API to above 279 µm.

The matching of particles size distribution of the API and diluent is considered one factor influencing the herein disclosed robust process and reproducible encapsulation of pimavanserin, e.g. 10-34 mg pimavanserin in size 4 capsules, e.g. two-piece capsules.

In some embodiment bulk density between the API and the diluent and optionally the lubricant are matched, for example granulated pimavanserin having a bulk density above >0.40 g/ml, such as about 0.5 g/ml, and the diluent 0.35-0.46 g/ml.

In some embodiments both the bulk density and the particle size distribution is used in combination in order to adequately match at least the pimavanserin granulate and the diluent in order to obtain capsules of size 4 comprising 10-34 mg pimavanserin.

In some particular embodiments the granulation of pimavanserin may be completed and the obtained pimavanserin granulation having suitable properties for the herein disclosed manufacturing process, in the absence of a binder. It is however possible to include a binder in the granulation but for various reasons not necessarily preferred.

In some embodiments disclosed herein the blended pimavanserin composition, as described herein, comprised in a capsule (e.g a size 4 capsule) have an average Specific Energy (SE) of less than 5 mJ/g, such as less than 4.5 mJ/g, such as less than 4 mJ/g, as obtained by FT4 measurement.

In some embodiments disclosed herein the blended pimavanserin composition, as described herein, comprised in a capsule (e.g a size 4 capsule) have an average Flow Rate Index (FRI) of 0.9-1.2, such as 1.0-1.1, as obtained by FT4 measurement.

In some embodiments disclosed herein the blended pimavanserin composition, as described herein, comprised in a capsule (e.g a size 4 capsule) have an average Specific Energy (SE) of less than 4.5 mJ/g, and an average Flow Rate Index (FRI) of 0.9-1.2.

Pharmaceutical Formulations

Some embodiments include a pharmaceutical composition comprising granulated pimavanserin tartrate, Form C which may include a small percentage of Form A, including a pharmaceutically acceptable diluent, binder or excipient, or combination thereof.

The pharmaceutical compositions disclosed herein, are in some embodiments, provided as a two-piece hard shell capsules made of gelatin (fish, mammalian, or vegetable sourced) or other combinations. The two-piece hard shell capsules may contain the pimavanserin granules with a filler/diluent and/or lubricants.

The finished dosage forms may be presented in packaging containing metal or plastic foil such as a blister pack. The pack may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription of drugs, or the approved package insert.

WO 2007/133802 discloses that only certain components are compatible with pimavanserin, and although certain components are compatible their use in the herein disclosed capsule may not be preferred. A particular example is lactose as it may have implications to the administration to subject being lactose intolerant.

Some requirements of the pharmaceutical manufacturing for pimavanserin are commercial operational speed, as well as stringent regulatory requirements. For example, the encapsulation equipment used is capable of ~100,000 capsules per hour, such as 40,000-90,000 capsules per hour, such as 60,000-86,000 capsules per hour, such as 60,000-70,000 capsules per hour. The manufacturing must be reproducible and robust to be capable of this output while producing quality product.

Prior to the surprising finding, i.e. the herein disclosed processes and compositions resulting in a robust and reliable filling of 5-34 mg pimavanserin in capsules of size 3 or 4, such as size 4 capsules, many experiments were done.

Comparative experiments resulting in unacceptable products

For example, the pharmaceutical industry has used fluid-bed layering extensively for several decades to produce small spherical particles with improved properties (e.g. flowability and compressibility) for further downstream processing, such as capsule filling. During this two-phase process that includes simultaneous spraying and drying, the addition of a binder causes primary particles to increase the diameter of the substrate by the addition of a dense layer of the drug and a binder, one such technique evaluted was top spray layering (use of conventional top-spray fluidized bed granulation equipment to apply the drug layer to a small substrate particle), e.g. using the following compostion about 63% w/w microcrystalline cellulose (the spherical particle (bead) around which the API is layered or applied), about 28% w/w of pimavanserin tartrate (API), about 6% w/w povidone (binder), such as povidone K30, and about 2% w/w HPMC E5 (Methocel™ E5) (hydroxypropylmethyl cellulose). The top spray fluid-bed layering resulted in particles having an acceptable flow and bulk density but unacceptable stability and particle size distribution as well an unacceptable amount of impurities. These unacceptable disadvantages, such as unacceptable stability, less favourable dissolution, resulted in deeming this process option unsuitable for the current purpose.

Wurster Layering (a similar and more common process to the Top Spray Layering described above) was tested and found to produce particles having an acceptable flow and bulk density but unacceptable stability and particle size distribution as well an unacceptable amount of impurities. These unacceptable disadvantages, such as unacceptable stability, less favourable dissolution, resulted in deeming this process option unsuitable for the current purpose. One compostion tested was the same as in the top spray layering.

Extrusion/spheronization is especially useful in producing semi-spherical, dense granules. The physical advantages of extrusion/spheronization vs. other multiparticulate approaches can include relatively high drug loading, improved flow properties, narrow particle size distribution, smooth and a coatable surface, low friability, and uniform packing characteristics. The process consists of five operations, i.e. wet granulating the formulation, followed by screening to form cylindrical extrudates, adding the extrudate to a spheronizer forming spheres from the extrudate, and drying the spheres. Optionally coatings may be applied to the spheres. A composition containing about 27% w/w pimavanserin tartrate as a 32% w/w slurry in water, about 68% w/w microcrystalline cellulose (e.g. Avicel PH 101), about 4% hydroxypropylmethyl cellulose (e.g. Methocel™ A15LV), and about 1% w/w povidone (e.g. povidone K30) resulted in particles having an acceptable flow and bulk density but unacceptable stability and particle size distribution as well an unacceptable amount of impurities. The particles were milled in order to achieve a uniform particle size, yet the amount of impurities and stability were found to be unacceptable.

Twin-Screw Melt Granulation has increased in popularity in pharmaceutical manufacturing due to the numerous advantages of this continuous manufacturing technique over traditional batch wet granulation. Twin-Screw Melt Granulation does not require the use of organic or aqueous solvents, making the entire process less consuming in terms of time and energy as compared to wet granulation, and in view of other tests disclosed hereinabove the use of solvent was deemed as a potential source for the impurities and may have been a factor for the stability issues observed. Consequently Twin-Screw Melt Granulation was evaluated using a binder/disintegrant, heat and agitation. As binder/disintegrant a low substituted hydroxypropyl cellulose (e.g. LH-B1 marketed by Shin Etsu), and Kollidon® VA64 marketed by BASF were used in separate compositions using about 50% w/w pimavanserin tartrate and LH-B1 and Kollidon VA64 respectively. In either case the resulting particles were screened and evaluated resulting in particles having an acceptable flow and bulk density but unacceptable finding of impurities as well as unacceptable dissolution.

Conventionally wet granulation (both high shear and low shear) have been used for a long time in pharmaceutical manufacturing, an example of a conventional wet granulation process is described in WO2009/061909 wherein table 7 discloses 40-50% w/w of water being used in the wet granulation, i.e. conventionally a wet granulation uses a liquid, e.g. water in order to prepare a wet mass with sufficient plasticity which can be subsequently wet-milled and dried produce granules with improved flow and density properties. High shear granulation was chosen for evaluation due to the higher energy it is capable of imparting to the particles, which was known to improve the particle density, spherocity, and consequently the capsule filling capability and particle flow, respectively. The quantity of water used in conventional or traditional wet granulation proved to be problematic resulting in very large, wet, adhesive pimavanserin granules that would not be easily dried in a fluid bed dryer. Additionally, large quantity of water would also result in high impurities and changes in the crystallinity of pimavanserin.

Several embodiments were evaluated using excipients commonly used to mitigate the impact of high water content while providing excellent granule properties. These did not improve the resulting over-wetting of the pimavanserin blend and resulted in an adhesive wet mass that would not would not be easily dried in a fluid bed dryer.

Contrary to the above disclosed comparative experiments the present application describes processes to manufacture capsules of size 4 comprising 5-34 mg pimavanserin. As additionally disclosed above it was surprisingly found that a 100% pimavanserin high-shear granulation was possible by using only small water quantities, often large quantities of water and a binder conventionally used in high-shear granulation. In order for a small quantity of water to be effective, the distribution of the water should be finely divided providing small points of localized wetting of pimavanserin. Localized wetting is considered wetting of an immediate area around the water droplets. Examples of suitable size of the water droplets to be sprayed are about 0.05-0.15 mm The granulation of pimavanserin, for example without the presence of a binder, was achieved using a small amount of water and a nozzle, such as an atomizing nozzle, capable of producing a spray pattern that covered a large area of pimavanserin and preventing over-wetting of large areas of the batch. Suitable nozzles are commercially available, e.g. from Spraying Systems Co. Spraying of low amounts of water and appropriate impeller speed and chopper speed of the high shear granulator achieved pimavanserin granulation having altered properties and improved the flow, e.g. bulk density compared to the native API. The total quantity of water added to the pimavanserin granulation should be limited to a global value the would not result in a global state of over-wetting (global refers to a large area of the batch being over-wetted), which as described above would occur during conventional wet granulation of pimavanserin, causing an adhesive wet mass that would not be easily dried in a fluid bed dryer, i.e. not resulting in a sufficiently dried product, or too long drying times, and increasing the risk of changing the crystalline form of pimavanserin (e.g. changing pimavanserin into amorphous forms), which could result in slow dissolution when administered to a patient. As disclosed above conventionally high shear granulation utilizes amounts of water that would lead to over wetting of an API, such as pimavanserin, and the present inventors have demonstrated that an appropriate water application, e.g. using a nozzle, capable of spraying water over a large area of the API, combined with a chopper/impeller speed (e.g. by controlling amperage), results in granulated pimavanserin having improved bulk density suitable for filling amounts disclosed herein into capsules of size 4.

In addition to the global, or batch, over-wetting a local over-wetting may also impair the properties of the API. One solution presented herein relates to applying a spray of water having a droplet size such as 0.05-0.15 mm, e.g. using a nozzle spraying the water and resulting in adequate wetting, locally and globally.

Suitable drying times of the wet granulation described herein is 120 min, such as 100 min, such as 80 min, such as 60 min. A drying time of 60 min is preferred, e.g. in view of process efficiency etc. The global quantity of water will vary depending on many factors such as the capacity of the high shear granulator, loading of the high shear granulator, the batch of pimavanserin to be granulated, surrounding environment, and may be controlled by impeller speed and chopper speed as well as the spray rate and spray pattern parameters (e.g. using a atomization nozzle), and the amperage (energy consumption) of the granulator. As the high shear granulator is an "open" system and energy from the impeller actually incorporates into the product causing the product temperature to increase favorably limiting the global impact of the added water when applied at a low rate. However, the range of water was found to be approximately 3-15% w/w, such as 3-10% w/w, such as 3-8% w/w (based on the mass of the pimavanserin in the granulator at the start of the granulation process). As disclosed herein it has been demonstrated that pimavanserin can be granulated without the use of a binder, i.e. utilizing water only. It is however contemplated that in some embodiments suitable binders, such as cellulose, methyl cellulose, polyvinylpyrrolidone and polyethylene glycol may be used, although not a necessity. The present high shear granulation of pimavanserin utilizing e.g. 3-8% w/w water, applied by an nozzle, which can generate an atomized spray pattern, provides benefits.

Embodiments disclosed herein relate to pimavanserin tartrate as crystalline Form C, Form A or a combination thereof.

The doses referred to herein, i.e. 5-34 mg refers to pimavanserin free base (equivalent to about 6 mg-40 mg pimavanserin tartrate).

Some embodiments relates to pimavanserin tartrate Form C (40 mg of pimavanserin tartrate, equivalent to 34 mg pimavanserin free base) being encapsulated in capsules of size 3 or 4, such as capsules of size 4.

One embodiment of the compositions described herein includes pimavanserin tartrate granulation without binder, dried, and thereafter blended with less than 60% w/w microcrystalline cellulose such as Avicel PH302 or equivalent microcrystalline cellulose, and about 1% w/w magnesium stearate.

In some embodiments the compositions described herein comprises granulated pimavanserin and microcrystalline cellulose is at least 20% w/w microcrystalline cellulose, such as 30% w/w microcrystalline cellulose, such as 40% w/w microcrystalline cellulose, such as 50% w/w microcrystalline cellulose, such as 50-89% w/w microcrystalline cellulose, such as 20-94% w/w, such as 50-94% w/w, such as 57-94% w/w, such as 57-89% w/w microcrystalline cellulose, such as 57-79% w/w microcrystalline cellulose, or 57-60% w/w microcrystalline cellulose, or 57-59.5% w/w microcrystalline cellulose, or 58.5-59.5% w/w microcrystalline cellulose, or 59% w/w microcrystalline cellulose.

In some embodiments the compositions described herein comprises granulated pimavanserin and microcrystalline cellulose and magnesium stearate, such as 0.1-3% w/w, such as 0.5-2% w/w magnesium stearate, or 0.5-1.5% w/w magnesium stearate, or 1% w/w magnesium stearate.

In some embodiments the compositions described herein comprises granulated pimavanserin (5, 10, 20 or 34 mg) and microcrystalline cellulose is at least 20% w/w microcrystalline cellulose, such as 30% w/w microcrystalline cellulose, such as 40% w/w microcrystalline cellulose, such as 50% w/w microcrystalline cellulose, such as 50-89% w/w microcrystalline cellulose, such as 20-94% w/w, such as 50-94% w/w, such as 57-94% w/w, such as 57-89% w/w microcrystalline cellulose, such as 57-79% w/w microcrystalline cellulose, or 57-60% w/w microcrystalline cellulose, or 57-59.5% w/w microcrystalline cellulose, or 58.5-59.5% w/w microcrystalline cellulose, or 59% w/w microcrystalline cellulose and magnesium stearate, such as 0.1-3% w/w, such as 0.5-2% w/w magnesium stearate, or 0.5-1.5% w/w magnesium stearate, or 1% w/w magnesium stearate.

The compositions disclosed herein comprise pimavanserin and additional compatible excipients, e.g. sugars, sucrose, mannitol, sorbitol, polysaccharides (e.g. from corn, wheat, rice, potato), as well as pregelatinized or partially pregelatinized starches (e.g. STARCH 1500®), cellulose preparations such as microcrystalline cellulose (MCC) (e.g. AVICEL® PH 302, AVICEL® PH 102, VIVAPUR® 302, VIVAPUR® 102, EMCOCEL® HD 90), silicified microcrystalline cellulose (e.g. PROSOLV® 50, PROSOLV® 90, PROSOLV® HD90), lactose cellulose blends (e.g. CELLATOSE® 80, CELLATOSE® 90, PROSOLV® EASYtab SP), hydroxypropylmethyl cellulose, hydroxymethyl cellulose, polyvinylpyrrolidone, lubricants such as magnesium stearate, sodium stearyl fumarate, colloidal silicon dioxide, and talc.

Several tests attempting to mitigate the impact of the high water quantity used in high-shear granulation by the use of excipients generally capable of absorption of the water were made. However, these proved to be unsuccessful.

One embodiment of the compositions described herein includes pimavanserin tartrate granulation without binder, drying, and blending said granulation with microcrystalline cellulose having a bulk density of 0.35-0.46 g/ml, and wherein the bulk density of the blended composition is >0.4 g/ml, such as >0.5 g/ml.

In some embodiments the composition comprises microcrystalline cellulose (MCC) having a bulk density of about 0.40 g/ml, such as 0.3-0.5 g/ml, such as 0.35-0.46 g/ml. In some embodiment the API having a bulk density of >0.40 g/ml and MCC having a bulk density of 0.30-0.50 g/ml and is blended with magnesium stearate in order to make up a composition having a bulk density of 0.40-0.55 g/ml.

One embodiment of the compositions described herein includes pimavanserin tartrate granulation with spraying water and without any binder, followed by, drying, and blending said granulation with less than 50% w/w microcrystalline cellulose such as Avicel PH302 or equivalent microcrystalline cellulose, and about 1% w/w magnesium stearate. The spraying of water to pimavanserin tartrate is done while mixing in an appropriate granulator.

Another embodiment of the composition described above includes pimavanserin tartrate granulation containing less than 10% w/w Avicel PH302 and colloidal silicon dioxide, e.g. Aerosil Pharma 200 manufactured by Evonik, with a specific surface area from about 175 to about 225 $m^2/g$ blended with less than 60% w/w microcrystalline cellulose, such as Avicel PH302 or equivalent microcrystalline cellulose, and about 1% w/w magnesium stearate.

Another embodiment of the composition described above includes pimavanserin tartrate granulation containing less than 10% w/w Avicel PH101 and colloidal silicon dioxide with a specific surface area from about 175 to about 225 $m^2/g$, e.g. Aerosil Pharma 200 manufactured by Evonik, blended with less than 60% w/w microcrystalline cellulose, such as Avicel PH302 or equivalent thereof, and about 1% w/w magnesium stearate.

As used herein, whenever a USP is referred to it is the current official version at the time of filing of the application, i.e 40-NF 35, released Nov. 1, 2016 and official May 1, 2017.

Provided herein are embodiment for manufacturing pimavanserin granulation comprising: providing pimavanserin and adding water while mixing in an appropriate granulator, such as a high shear granulator; granulating and; drying the wet pimavanserin granulation, sizing the pimavanserin granulation, e.g. through a screen, such as a 10-20 mesh screen; and obtaining pimavanserin granulation. Said pimavanserin granulation being suitable for encapsulation in size 4 capsules, for example by blending with a diluent before capsule filling (encapsulation).

Provided herein are embodiment for manufacturing pimavanserin granulation by: providing pimavanserin (weighed and the loss-on-drying (LOD) moisture content determined) to a high shear granulator; pre-blending (optional); providing granulation water, e.g. 3-8% w/w, e.g. by spraying at a controlled rate and/or a controlled pattern (e.g. using an atomization nozzle) while monitoring the impeller speed and/or amperage, and granulating; stopping the provision of granulation water, e.g. when the impeller amperage increases; wet massing, e.g. without changing the impeller speed; drying the wet granulation, e.g. in a fluid bed dryer until the LOD moisture is at or below the LOD moisture of the pimavanserin as provided; and sizing, e.g. through a 10-mesh screen; and obtaining pimavanserin granulation. Said pimavanserin granulation being suitable for encapsulation in size 3 or 4 capsules, for example by providing additional excipients during the screening, followed by filling of the capsule.

It is important to control the amount of water, the water application rate and/or water application method thereof (e.g. using an atomization nozzle, or another suitable spraying device) as too much water may have a negative impact, e.g. change its properties, such as its crystallinity, of pimavanserin. Adding too much water, e.g. 25% w/w, would have undesired effects on properties of pimavanserin, which would cause issues with the continued pharmaceutical manufacturing of capsules. In some embodiments water is sprayed (e.g. using an atomization nozzle) to pimavanserin while mixing. Addition of water without mixing may lead to localized over-wetting. Provided herein are embodiments wherein pimavanserin, for example pimavanserin tartrate, such as pimavanserin tartrate Form C, is granulated with water using high shear granulation. In some embodiments the amount of water is 1-10% w/w (water based on dry ingredient content), such as 3-8% w/w. In some embodiments the impeller speed and/or chopper speed of the high shear granulator is controlled in order to obtain a granulation of sufficient quality for further processing. The wet granulation is then dried, e.g. in fluid bed dryers or tray dryers at controlled conditions of temperature and drying air flow. The dried granulation is then sized using a screening mill or other appropriate milling (delumping), and blended with appropriate pharmaceutical diluents and/or binders, such as microcrystalline cellulose, enabling the filling of 5-34 mg granulated pimavanserin (equivalent to about 6 mg-40 mg pimavanserin tartrate) in a size 3 (0.30 ml volume) or 4 (0.21 ml volume) capsule. Some embodiments relates to the capsule being a capsule of size 4, and a two-piece capsule.

Provided herein is a process for manufacturing capsules containing 5-34 mg pimavanserin; by providing pimavanserin, for example pimavanserin tartrate, such as pimavanserin tartrate Form C and water, e.g. 1-10% w/w, such as 2-9% w/w, such as 3-8% w/w, such as 4-8% w/w, such as 5-8% w/w, such as 5-7% w/w to a high shear granulator, granulating pimavanserin and the water, drying the pimavanserin granulation, sizing (or screening, may also be referred to as delumping) the dried pimavanserin granulation, e.g. using a screening mill, blending with one or more pharmaceutical excipients, such as one or more filler (diluent) filling a size 3 or 4 capsule, e.g. a two-piece capsule, with pimavanserin granulation. Provided herein is a process for manufacturing capsules containing 5-34 mg pimavanserin, wherein the process comprises the following (e.g. in said order): providing pimavanserin, for example pimavanserin tartrate, such as pimavanserin tartrate Form C to a high shear granulator, granulating pimavanserin together with water (e.g. 1-10% w/w, such as 2-9% w/w, such as 3-8% w/w, such as 4-8% w/w, such as 5-8% w/w, such as 5-7% w/w) while controlling the water application rate, and/or atomization parameters (e.g. by using an appropriate nozzle such as an externally mixed, two-fluid, air-atomizing spray nozzle), impeller speed (e.g. by monitoring amperage), and/or chopper speed (e.g. by monitoring amperage), drying the granulated pimavanserin, e.g. using fluid bed drying, sizing the dried pimavanserin granulation, e.g. using a screening mill or other appropriate milling device (such as oscillating mills, impact mills), blending the sized pimavanserin granulation with one or more filler/diluent (optionally including a lubricant), and final blending with a lubricant (unless the filler/diluent includes a lubricant), filling a size 3 or 4 two-piece capsule with the blended pimavanserin composition. In some embodiments the capsule is a capsule of size 4 and the amount of pimavanserin is 34 mg. As specified herein, such as hereinbelow, excipients such as diluents, binders, lubricants, pharmaceutical flow agents, and/or other excipients compatible with pimavanserin may be included. Some embodiments provide pimavanserin, microcrystalline cellulose and magnesium stearate only. Some embodiements relate to the microcrystalline cellulose having a particle size distribution (D90) of 180-340 µm. Some embodiments relate to microcrystalline cellulose having a bulk density above >0.40 g/ml. Some embodiements relate to the microcrystalline cellulose having a particle size distribution (D90) of 180-340 µm and a bulk density above >0.40 g/ml.

Provided herein are embodiments wherein the capsule is a capsule of size 4, e.g. a two-piece capsule, such as a two-piece hard shell capsule, e.g. a two-piece capsule of gelatin or hydroxypropyl methylcellulose (HPMC). Some commercial examples are VCaps®, VCaps® Plus, Coni-Snap® marketed by Capsugel.

Provided are also embodiments wherein pimavanserin (granulated), microcrystalline cellulose, for example Avicel PH302 or an equivalent microcrystalline cellulose, and/or magnesium stearate, for example vegetable grade are encapsulated in a capsule of size 4, for example a two-piece capsule.

Provided are also embodiments wherein 34 mg pimavanserin (granulated) (equivalent to 40 mg pimavanserin tartrate), microcrystalline cellulose, such as microcrystalline cellulose having a particle size distribution (D90) of 180-340 µm, for example Avicel PH302 or an equivalent microcrystalline cellulose, and/or magnesium stearate, for example vegetable grade are encapsulated in a capsule of size 4, for example a two-piece capsule.

Provided are also embodiments wherein 10 or 20 mg pimavanserin (granulated), microcrystalline cellulose, for example Avicel PH302 or an equivalent microcrystalline cellulose, and/or magnesium stearate, for example vegetable grade are encapsulated in a capsule of size 4, for example a two-piece capsule.

Provided are also embodiments wherein 34 mg pimavanserin (granulated), 59 mg microcrystalline cellulose, for example Avicel PH302 or an equivalent microcrystalline cellulose, and/or 1 mg magnesium stearate, for example vegetable grade are encapsulated in a capsule of size 4, for example a two-piece capsule. No other excipients were added.

Also provided is a pharmaceutical composition, comprising a capsule of pimavanserin and one or more pharmaceutically acceptable excipient(s) as provided herein, wherein the composition is formulated such that at least 80% of pimavanserin is released in 30 minutes upon administration to a subject.

Also provided is a pharmaceutical composition, comprising a capsule of pimavanserin and one or more pharmaceutically acceptable excipient(s) as provided herein, wherein the composition is formulated such that at least 80% of the pimavanserin is released from the composition within 30 minutes upon in vitro dissolution testing according to USP<711> (apparatus 1 (basket apparatus)).

The final moisture content of the pimavanserin granulation is equivalent to the starting moisture content of the pimavanserin.

Another requirement achieved by the pimavanserin capsules disclosed herein can be a long shelf-life, i.e., a shelf-life of at least 1 year is obtained, such as 2 years of shelf-life.

Examples

Manufacturing of a capsule, size 4 two-piece capsule, comprising 34 mg pimavanserin equivalent to 40 mg pimavanserin tartrate Pimavanserin 34 mg capsules may be prepared as outline herein below.

Granulation: The required ingredients for all operations of the entire process are weighed. The loss-on-drying (LOD) moisture content of the pimavanserin is determined, for example using an appropriate LOD instrument such as those manufacture by Mettler, Ariz. Instruments, Ohaus or Denver Instruments. Drying end point may be determined using temperature, time or weight loss. Pimavanserin is charged through a screen (25-40 mesh) into a high shear granulator, for example a Glatt Powerex 50 liter high shear granulator equipped with a 25 liter bowl. Following a pre-blend in the high shear granulator (200-400 rpm), granulation water, e.g. 5-8% w/w is sprayed at a controlled rate ((18.5-26.5 g/min) at 15 psi (10.0-20.0) atomization air pressure while monitoring the impeller speed ((200-400 rpm)) and amperage, chopper speed (1600-2000 rpm). When the impeller amperage increases (such as 13-18%,), the spray of water is stopped and the mixture wet massing for 5 minutes without changing the impeller or chopper speeds. Following the 5-minute wet massing, the wet granulation is discharged and placed in a fluid bed dryer (100-140 cfm; 45-55° C.); dew point 10° C.; filter shaking 15 sec/5 sec (interval/duration) until the LOD moisture is at or below the LOD moisture of the pimavanserin at dispensing. The dried granulation is discharged from the fluid bed dryer, screened through a screen (4-12 mesh), and packaged until diluent blending and encapsulation.

Diluent Blending: The screened, dried pimavanserin granulation is dispensed (weighed) for blending/encapsulation unit operations. The required diluent and lubricant quantities are also dispensed. The dispensing is followed by delumping of pimavanserin granulation with a screening mill such as 197S or U10 Comil equipped with a screen (4-12 mesh) at 2300-2500 rpm, blending of the granulation with diluent using a bin type blender such as 2 liter TOTE blender 20 minutes at 19-21 rpm or other appropriate blender, final blending with lubricant using the same bin type blender or other appropriate blender (3 minutes at 19-21 rpm) , and encapsulation using a IIM 2100 equipped with size 4 change parts and 5-12 mm dosing disk (50-90 segments per minute (spm)).

Optionally low shear granulation such as a V-Blender equipped with an intensifier bar, twin screw granulation, may be used instead of the granulation equipment specified above with appropriate adjustment to the milling/screening parameters to manufacture capsules of pimavanserin Pimavanserin hard shell capsules (34 mg pimavanserin, equivalent to 40 mg pimavanserin tartrate) were manufactured. Table 2 contains an example of a suitable formulation.

As an alternative, the herein disclosed pimavanserin granulation may be compressed as a tablet.

As an alternative, the herein disclosed pimavanserin granulations may be compressed as a tablet without further excipients. Thus the composition disclosed in table 2 in some embodiments is used to form tablets. Said tablets may be formed as an alternative to the filling of a capsule.

Consequently the obtained pimavansering granulation may be compressed into a tablet of a weight of about 100 mg.

TABLE 2

Composition of Pimavanserin granulation (34 mg)

| Ingredients | Qty (% w/w) | Qty (mg)/dose |
|---|---|---|
| Pimavanserin Tartrate | 40.0 | 40.0[a] |
| Microcrystalline Cellulose (Avicel PH302, NF, EP) | 59.0 | 59.0 |
| Magnesium Stearate (Vegetable Source, USP, EP) | 1.0 | 1.0 |
| Total | 100.0 | 100.0 |

[a] 40 mg pimavanserin tartrate salt is equivalent to 34 mg pimavanserin free base Table 3 contains the manufacturing process equipment for pimavanserin capsules, 34 mg.

TABLE 3

| Process Step | Equipment class, sub-class | Manufacturer, model, size |
|---|---|---|
| Screening I (API) | Hand screen | 30 Mesh hand screen |
| Granulation | Vertical granulator | Glatt/Powrex VG-50M with 25 L Bowl |
| Fluid Bed Drying | Fluid bed | Glatt GPCG-5 with 25 L bowl |
| Screening II (granulation) | Hand screen | 10 Mesh hand screen |
| Milling | Screening mills, rotating impeller | Comil 197S or U10 with 045R03125 screen |
| Blending I | Diffusion mixers (Tumble), bin blender | TOTE Bin blender, 2 cubic foot |
| Screening III (Magnesium stearate) | Hand screen | 30 Mesh hand screen |
| Final Blending | Diffusion mixers (Tumble), bin blender | TOTE Bin blender, 2 cubic foot |
| Encapsulation | Encapsulator, dosing disk | IIM 2100, Size 4 change parts and 10 mm dosing disk |
| Polishing and weight checking | Not applicable | Bosch KKE 1500 |

Table 4 outlines the process parameters and ranges for pimavanserin capsules, 34 mg manufacture. Bold references are target values with the ranges displayed in parenthesis.

TABLE 4

| Process Step: Equipment | Process Parameter | Ranges |
|---|---|---|
| Screening I (API) 25-40 Mesh hand screen | Screen size | 25-40 Mesh hand screen |
| Granulation Glatt/Powrex VG-50M with 25 L bowl | Spray rate | (10-50) [g/min] |
| | Impeller speed | (200-400) [rpm] |
| | Chopper speed | (1600-2000) [rpm] |
| | Atomization Air Pressure | (3-20) [psig] |
| Fluid Bed Drying Glatt GPCG-5 with 25 L bowl | Process Air Volume | (90-210) [cfm] |
| | Inlet Air Temperature | (40-60) [° C.] |
| Screening II (granulation) 4-12 Mesh hand screen | Screen size | 4-12 Mesh hand screen |
| Screening Blending I | Screen size Diffusion blender | 25-40 mesh |
| Screening (Magnesium stearate) | Screen size | 25-40 Mesh |
| Blending I | Diffusion blending | |
| Encapsulation dosing disk based encapsulator | Dosing disk | 5-12 mm |

In some embodiments disclosed herein relate to pimavanserin granulation, e.g. composed as in table 2, having a weight of granulation of 100 mg ±7 (average of 20 samples), i.e. the weight relates to the granulation only, i.e. excluding capsule shell weight.

The bulk density of the blended composition is >0.4 g/ml, such as 0.4-0.6 g/ml, such as about 0.5 g/ml determined according to USP <616>, method 1. In some embodiments the bulk density of the composition is >0.4 g/ml, such as about 0.5 g/ml, such as 0.51 g/ml, such as 0.508 g/ml.

The bulk density of pimavanserin granulation is >0.4 g/ml, such as 0.4-0.6 g/ml, such as about 0.5 g/ml, determined according to USP <616>, method 1. In some embodiments the bulk density of the pimavanserin granulation is >0.4 g/ml, such as about 0.5 g/ml, such as 0.51 g/ml, such as 0.508 g/ml.

In addition to the bulk density and Carr's Index obtained according to USP <616>, method 1, FT4 Powder Rheology was obtained for the API (pimavanserin tartrate) and for the compositions disclosed herein using a FT4 Powder Rheometer according to ASTM D7891-15; Standard Test Method for Shear Testing of Powders Using the Freeman Technology FT4 Powder Rheometer Shear Cell.

As discussed herein above the flowability of the composition has been improved compared to the API (pimavanserin tartrate), which for example can be supported by the Specific Energy (SE) obtained from the FT4 measurements. Specific Energy is a measure of the powder's flowability when unconfined, such as during low stress filling, or low shear blending. The average Specific Energy (SE) for the API is about 10.08+/−0.23 mJ/g. The granulated pimavanserin had an average SE of 6.81+/−0.63 mJ/g, and the blended pimavanserin composition an average SE of 3.96+/−0.36 mJ/g. Thus the unconfined flowability was substantially improved compared to the API.

In addition to SE, the Flow Rate Index (FRI) of the composition showed significant improvement compared to the API (pimavanserin tartrate). FRI indicates sensitivity to changing the rate of flow, and the pimavanserin tartrate had an average FRI of 1.90±0.01, the granulated pimavanserin an average FRI of 1.52+/−0.10, and the blended pimavanserin composition had an average FRI of 1.08±0.06, again showing the improved properties for the granulated pimavanserin as well as the blended pimavanserin composition for filling into a capsule of size 3 or 4.

The FT4 Powder Rheometer was also used as yet another means to compare the bulk density between the API, the granulated pimavanserin and the blended pimavanserin compositions disclosed herein and in the accompanying claims. The bulk density is a conditioned bulk density as obtained by the FT4 measurement, in accordance with ASTM D7891-15; Standard Test Method for Shear Testing of Powders Using the Freeman Technology FT4 Powder Rheometer Shear Cell. Pimavanserin tartrate (API) had an average conditioned bulk density (CBD) of 0.336±0.006 g/ml, granulated pimavanserin tartrate had an average conditioned bulk density (CBD) of 0.478±0.028 g/ml, and the blended pimavanserin composition an average CBD of 0.504±0.020 g/ml.

The conditioned bulk density of the blended composition is >0.45 g/ml, such as 0.45-0.6 g/ml, such as 0.47-0.55 g/ml determined according to ASTM D7891-15. In some embodiments the bulk density of the composition >0.45 g/ml, such as an average of about 0.5 g/ml.

The conditioned bulk density of the granulated pimavanserin is >0.42 g/ml, such as 0.42-0.55 g/ml, such as 0.43-0.53 g/ml determined according to ASTM D7891-15. In some embodiments the bulk density of the granulated pimavanserin >0.42 g/ml, such as an average of about 0.48 g/ml.

The blended pimavanserin composition used in the herein mention FT4 Powder Rheometry measurements comprised 34 mg pimavanserin, 59 mg microcrystalline cellulose and 1 mg magnesium stearate.

The capsules comprising 5-34 mg pimavanserin are stable upon actual or simulated storage under open conditions at 25° C.±2°/60%±5% (RH) relative humidity for at least 1 year, such as at least 1.5 years.

Alternative methods and equipment to be used in connection with the herein disclosed methods, compositions, capsules, tablets and disclosures may be found in SUPAC: manufacturing equipment addendum, an U.S. Department of Health and Human Services, Food and Drug Administration, Center for Drug Evaluation and Research (CDER) issued guidance for industry, e.g. in the December 2014 version, Pharmaceutical Quality/CMC.

The embodiments disclosed herein above meet all specifications outlined relating to the marketing authorization of Nuplazid®, for example:

Assay (90.0-110.0% of Label Claim), i.e. quantify the amount of pimavanserin free base in the drug product, for example using reverse phase HPLC with UV-detection at 210 nm. An example of eluent is a gradient comprised of two mobile phases such as ammonium buffer (pH 9.0), and acetonitrile/methanol (80/20 vol/vol).

Content Uniformity as determined using USP <905>, Uniformity of Dosage Forms and wherein the maximum Acceptance Value (AV) NMT (not more than) 15.0. The AV is calculated for the number of units tested; Level 1=10 units; Level 2=30 units using the following: the mean Assay value for the number of units tested Minus Either 98.5 (when the mean is less than 98.5% of target assay) and 101.5 (when the mean is greater than 101.5% of target assay) times 2.4 (10 units) or 2.0 (30 units) plus the difference between the Mean and the appropriate Upper/Lower % of target assay, using the method for hard capsules.

Dissolution USP <711>:
Stage 1: Q=80% within 30 minutes
Stage 2: Average of 12 units (Stage 1 & Stage 2) is equal to or greater than Q with no unit less than Q-15%

X-ray powder diffraction (XRPD) analyses on a Bruker AXS D8 Advance system with a Bragg-Brentano configuration using CuKα radiation confirmed that all XRPD patterns for the granulations correspond to the XRPD patterns of the currently approved NUPLAZID 17 mg tablet (pimavanserin tartrate form C), which for example as disclosed in U.S. 7,732, 615.

Long term stability data for capsules containing 34 mg pimavanserin, 59 mg microcrystalline cellulose and 1 mg magnesium stearate at 18 months were determined using standard procedures such as actual or simulated storage under open conditions at 25° C.±2°/60%±5% (RH) relative humidity, e.g. as outlined in WHO Technical Report Series, No. 953, 2009, Annex 2, and the following observations and determinations were made:

Appearance: unchanged at 18 months
Assay (90.0-110.0% of Label Claim): Day 8: 100±2%; 18 months: 100±2%
Total impurities: Day 0: 0.3%; 18 months: 0.3%, determined in line with Assay.
Dissolution (at 18 months): at least 80% of the pimavanserin is released from the composition within 30 minutes upon in vitro dissolution testing according to USP<711> (apparatus 1 (basket apparatus)).

Water content (determined in line with USP<921>, method I*a*: Day 0: 2.9%; 18 months: 2.9%.

What is claimed is:

1. A pharmaceutically acceptable capsule for orally delivering 34 mg of pimavanserin to a patient, wherein the capsule has a size 3 or 4 capsule shell that contains a blended pimavanserin composition comprising:
    granules comprising 40 mg pimavanserin tartrate and optionally one or more pharmaceutically acceptable excipients;
    and one or more blending excipients; wherein the bulk density of the granules is >0.4 g/ml as determined by USP<616>, method 1.

2. The pharmaceutically acceptable capsule of claim 1, wherein one of the blending excipients is selected from the group consisting of magnesium stearate, sodium stearyl fumarate, colloidal silicon dioxide, and talc.

3. The pharmaceutically acceptable capsule of claim 1, wherein the blended pimavanserin composition has a D90 particle size distribution of 60-450 μm as measured using laser scattering particle size analysis.

4. A pharmaceutically acceptable capsule for orally delivering 34 mg of pimavanserin to a patient, wherein the capsule has a capsule shell with a capsule shell size 3 or 4, that encapsulates a blended pimavanserin composition comprising:
    granules comprising 40 mg pimavanserin tartrate and one or more pharmaceutically acceptable excipients; and wherein the bulk density of the granules is >0.4 g/ml as determined by USP<616>, method 1.

5. The pharmaceutically acceptable capsule of claim 4, wherein the capsule shell is a hard shell size 4 capsule.

6. The pharmaceutically acceptable capsule of claim 1, wherein one of the blending excipients is selected from the group consisting of a cellulose, a polysaccharide, and polyvinylpyrrolidone.

7. The pharmaceutically acceptable capsule of claim 1, wherein one of the blending excipients is selected from the group consisting of microcrystalline cellulose, silicified microcrystalline cellulose, hydroxypropyl cellulose, hydroxypropylmethyl cellulose, hydroxymethyl cellulose, and a lactose cellulose blend.

8. The pharmaceutically acceptable capsule of claim 1, wherein the one of the blending excipients is selected from the group consisting of sucrose, mannitol, sorbitol, pregelatinized starch, and partially pregelatinized starch.

9. The pharmaceutically acceptable capsule of claim 1, wherein the blending excipients comprise microcrystalline cellulose and magnesium stearate.

10. The pharmaceutically acceptable capsule of claim 1, wherein the blending excipients are selected from the group consisting of filler/diluents, lubricants and mixtures thereof.

11. The pharmaceutically acceptable capsule of claim 1, wherein the granules comprise a pharmaceutically acceptable excipient which is a binder.

12. The pharmaceutically acceptable capsule of claim 10, wherein the binder is selected from the group consisting of cellulose, methyl cellulose, polyvinylpyrrolidone and polyethylene glycol.

13. The pharmaceutically acceptable capsule of claim 4 wherein the pharmaceutically acceptable excipients comprise a binder.

* * * * *

UNITED STATES PATENT AND TRADEMARK OFFICE
CERTIFICATE OF CORRECTION

| | | |
|---|---|---|
| PATENT NO. | : 11,452,721 B2 | Page 1 of 1 |
| APPLICATION NO. | : 17/693830 | |
| DATED | : September 27, 2022 | |
| INVENTOR(S) | : Ravindra Tejwani et al. | |

It is certified that error appears in the above-identified patent and that said Letters Patent is hereby corrected as shown below:

In the Claims

In Claim 12, at Column 24, Line 57, replace "capsule of claim 10" with --capsule of claim 11--.
In Claim 13, at Column 24, Line 62, replace "the pharmaceutically acceptable excipients" with --the one or more pharmaceutically acceptable excipients--.

Signed and Sealed this
Twelfth Day of August, 2025

Coke Morgan Stewart
*Acting Director of the United States Patent and Trademark Office*